(12) United States Patent
Warren et al.

(10) Patent No.: US 7,771,999 B2
(45) Date of Patent: *Aug. 10, 2010

(54) DISEASE MODEL INCORPORATION INTO AN ARTIFICIAL IMMUNE SYSTEM (AIS)

(75) Inventors: William L. Warren, Orlando, FL (US); Heather Fahlenkamp, Cleveland, OK (US); Russell G. Higbee, Orlando, FL (US); Eric M. Mishkin, Winter Springs, FL (US); Guzman Sanchez-Schmitz, Orlando, FL (US); Michael D. Rivard, Natick, MA (US); Santosh Pawar, Orlando, FL (US)

(73) Assignee: VaxDesign Corp., Orlando, FL (US)

( * ) Notice: Subject to any disclaimer, the term of this patent is extended or adjusted under 35 U.S.C. 154(b) by 290 days.

This patent is subject to a terminal disclaimer.

(21) Appl. No.: 12/047,107

(22) Filed: Mar. 12, 2008

(65) Prior Publication Data

US 2009/0011455 A1    Jan. 8, 2009

Related U.S. Application Data

(63) Continuation-in-part of application No. 11/453,003, filed on Jun. 15, 2006, now Pat. No. 7,709,256, which is a continuation-in-part of application No. 11/116,234, filed on Apr. 28, 2005.

(60) Provisional application No. 60/565,846, filed on Apr. 28, 2004, provisional application No. 60/643,175, filed on Jan. 13, 2005.

(51) Int. Cl.
*C12N 5/06* (2006.01)
(52) U.S. Cl. ........................ 435/372; 435/373
(58) Field of Classification Search .................. None
See application file for complete search history.

(56) References Cited

U.S. PATENT DOCUMENTS

| | | | |
|---|---|---|---|
| 5,008,116 A | 4/1991 | Cahn | |
| 5,160,490 A | 11/1992 | Naughton et al. | |
| 5,354,686 A | 10/1994 | Haberman | |
| 5,562,910 A | 10/1996 | Daynes et al. | |
| 5,725,856 A | 3/1998 | Hudziak et al. | |
| 5,739,001 A | 4/1998 | Brown et al. | |
| 5,750,329 A | 5/1998 | Quinn et al. | |
| 6,177,282 B1 | 1/2001 | McIntyre | |
| 6,274,378 B1 | 8/2001 | Steinman et al. | |
| 6,479,064 B1 | 11/2002 | Atala | |
| 6,835,550 B1 | 12/2004 | Estell et al. | |
| 2002/0155108 A1 | 10/2002 | Barbera-Guillem et al. | |
| 2003/0109042 A1 | 6/2003 | Wu et al. | |
| 2003/0147923 A1 | 8/2003 | Klaviniskis | |
| 2003/0199006 A1 | 10/2003 | Britz et al. | |
| 2003/0207287 A1 | 11/2003 | Short | |
| 2004/0009943 A1 | 1/2004 | Semple et al. | |
| 2004/0109876 A1 | 6/2004 | Yamamoto et al. | |
| 2004/0234510 A1 | 11/2004 | Mochitate | |
| 2005/0191743 A1 | 9/2005 | Wu et al. | |
| 2005/0229264 A1 | 10/2005 | Chang et al. | |
| 2005/0282148 A1* | 12/2005 | Warren et al. .................. 435/4 |
| 2006/0105454 A1 | 5/2006 | Son et al. .................... 435/325 |
| 2006/0270029 A1* | 11/2006 | Warren et al. ............... 435/325 |
| 2006/0275270 A1 | 12/2006 | Warren et al. | |
| 2007/0015136 A1 | 1/2007 | Sanchez-Schmitz et al. | |
| 2007/0026392 A1* | 2/2007 | Warren et al. .................. 435/5 |
| 2007/0141552 A1 | 6/2007 | Warren et al. | |
| 2007/0154956 A1 | 7/2007 | Warren et al. | |
| 2007/0178076 A1 | 8/2007 | Drake et al. | |
| 2007/0218054 A1 | 9/2007 | Sukumar et al. | |
| 2008/0008653 A1 | 1/2008 | Tew et al. | |

FOREIGN PATENT DOCUMENTS

| | | |
|---|---|---|
| EP | 0 358 506 | 9/1989 |
| EP | 1 437 147 | 9/2002 |
| EP | 1970444 A1 | 12/2006 |
| WO | WO 99/15629 | 4/1999 |
| WO | WO 99/43788 | 9/1999 |
| WO | WO99/49319 | 9/1999 |
| WO | WO 03/041568 | 5/2003 |
| WO | WO 03/050271 | 6/2003 |
| WO | WO 2004/031361 | 4/2004 |
| WO | WO2004/101773 | 11/2004 |
| WO | WO 2007/075979 | 7/2007 |
| WO | WO 2007/106559 | 9/2007 |
| WO | WO 2007/146267 | 12/2007 |

OTHER PUBLICATIONS

Sarradell et al. (2003) *Vet. Pathol.*, 40, 395-404.
Oehler et al. (2000) *Ann. Hematol.*, 79, 355-362.
Buchler et al. (2003) *Vaccine*, 21, 877-882.
Dubey et al. (2005) *J. Clin. Endocrin & Met.*, 90, 247-255.
Roos et al. (2005) *Expert Opin. Drug Metab. Toxicol.* 1, 187-202.
Boni et al. (2006) *Eur. J. Immunol.* 36, 3157-3166.
Caux et al. (1995) *J. Immunol.* 155, 5427-5435.
Moser et al. (2000) *Nature Immunol.* 1, 199-205.
Tan et al. (2005) *J. Leuk. Biol.* 78, 319-324.
Aydar et al. (2005) *J. Immunol.* 174, 5358-5366.
Tew et al. (2001) *Trends Immunol.* 22, 361-367.
Wu et al. (2008) *J. Immunol.* 180, 281-290.
Cayeux et al. (1999) *Eur. J. Immunol.* 29, 225-234.
Santini et al. (2000) *J. Exp. Med.* 191, 1777-1788.
International Search Report—PCT/US08/70107.
International Search Report—PCT/US06/048959.
International Search Report—PCT/US07/014826.

(Continued)

*Primary Examiner*—Michail A Belyavskyi
(74) *Attorney, Agent, or Firm*—Roylance, Abrams, Berdo & Goodman LLP

(57) ABSTRACT

The present invention relates to methods of constructing an integrated artificial immune system that comprises appropriate in vitro cellular and tissue constructs or their equivalents to mimic the tissues of the immune system in mammals. The artificial immune system can be used to test the efficacy of vaccine candidates and other materials in vitro and thus, is useful to accelerate vaccine development and testing drug and chemical interactions with the immune system, coupled with disease models to provide a more complete representation of an immune response.

18 Claims, 10 Drawing Sheets

OTHER PUBLICATIONS

International Search Report—PCT/US08/69172.

Suematsu, et al., "Generation of a Synthetic Lymphoid Tissue-Like Organoid in Mice", Nature Biotechnology, vol. 22, No. 12, pp. 1539-1545 (Dec. 2004).

Randolph, et al., "Role of Tissue Factor in Adhesion of Mononuclear Phagocytes to and Trafficking Through Endothelium in Vitro", Blood, vol. 92, pp. 4167-4177 (1998).

Randolph, et al., "Differentiation of Monocytes into Dendritic Cells in a Model of Transendothelial Trafficking", Science, vol. 282, pp. 480-483 (1998).

Randolph, et al., "A Physiologic Function for p-Glycoprotein (MDR-1) During the Migration of Dendritic Cells from Skin Via Afferent Lymphatic Vessels", Proc. Natl. Acad. Sci., vol. 95, pp. 6924-2929 (1998).

Randolph, et al., "The CD16(+) (FcγRIII(+)) Subset of Human Monocytes Preferentially Becomes Migratory Dendritic Cells in a Model Tissue Setting", J. Exp. Med., vol. 196, No. 4, pp. 517-527 (2002).

Randolph, et al., "Mononuclear Phagocytes Egress from an In Vitro Model of the Vascular Wall by Migrating Across Endothelium in the Basal to Apical Direction: Role of Intercellular Adhesion Molecule I and the CD11/CD18 Integrins", J. Exp. Med., vol. 183, pp. 451-462 (1996).

Randolph, et al., "A Soluble Gradient of Endogenous Monocyte Chemoattractant Protein-1 Promotes the Transendothelial Migration of Monocytes In Vitro", The Journal of Immunology, vol. 155, pp. 3610-3618 (1995).

Furie, et al., "Migration of Neutrophils Across Endothelial Monolayers is Stimulated by Treatment of the Monolayers with Interleukin-1 or Tumor Necrosis Factor-Alpha", The Journal of Immunology, vol. 143, pp. 3309-3317 (1989).

Robbiani, et al., "The Leukotriene C4 Transporter MRP 1 Regulates CCL19 (MIP-3β, ELC)-Dependent Mobilization of Dendritic Cells to Lymph Nodes", Cell, vol. 103, pp. 757-768 (2000).

Podgrabinska, et al., "Molecular Characterization of Lymphatic Endothelial Cells", Proc. Natl. Acad. Sci. U.S.A., vol. 99, No. 25, pp. 16069-16074 (2002).

Berman, et al., "Roles of Platelet/Endothelial Cell Adhesion Molecule-1 (PECAM-1, CD31) in Natural Killer Cell Transendothelial Migration and Beta 2 Integrin Activation", The Journal of Immunology, vol. 156, pp. 1515-1524 (1996).

Gergel, et al., "Activation of Endothelium by Borrelia burgdorferi In Vitro Enhances Transmigration of Specific Subsets of T Lymphocytes", Infection and Immunity, vol. 69, pp. 2190-2197 (2001).

Qu, et al., "Autocrine Type 1 IFN and Contact with Endothelium Promote the Presentation of Influenza A Virus by Monocyte-Derived APC", The Journal of Immunology, vol. 170, pp. 1010-1018 (2003).

Mellman, et al., "Dendritic Cells: Specialized and Regulated Antigen Processing Machines", Cell. vol. 106, pp. 255-258 (2001).

Lukas, et al., "Human Cutaneous Dendritic Cells Migrate Through Dermal Lymphatic Vessels in a Skin Organ Culture Model". The Journal of Investigative Dermatology, vol. 106, pp. 1293-1299 (1996).

Fransson, et al., "Culture of Human Epidermal Langerhans Cells in a Skin Equivalent", British Journal of Dermatology, vol. 139, pp. 598-604 (1998).

Banchereau, et al., "Immunobiology of Dendritic Cells", Annu. Rev. Immunol., vol. 18, pp. 767-811 (2000).

Butcher, et al., "Lymphocyte Trafficking and Regional Immunity", Advances in Immunology, vol. 72, pp. 209-253 (1999).

Sprent, et al., "Antigen-Induced Selective Recruitment of Circulating Lymphocytes", Cellular Immunology, vol. 2, pp. 171-181 (1971).

Garside, et al., "Visualization of Specific B and T Lumphocyte Interactions in the Lymph Node", Science, vol. 281, pp. 96-99 (1998).

Jenkins, et al., "In Vivo Activation of Antigen-Specific CD4 T Cells", Annu. Rev. Immunol., vol. 19, pp. 23-45 (2001).

Kaldjian, et al., "Spatial and Molecular Organization of Lymph Node T Cell Cortex: A Labyrinthine Cavity Bounded by an Epithelium-Like Monolayer of Fibroblastic Reticular Cells Anchored to Basement Membrane-like Extracellular Matrix", International Immunology, vol. 13, pp. 1243-1253 (2001).

Gretz, et al., "Sophisticated Strategies for Information Encounter in the Lymph Node: The Reticular Network as a Conduit of Soluble Information and a Highway for Cell Traffic", The Journal of Immunology, vol. 157, pp. 495-499 (1996).

Van Den Berg, et al., "Localization of β1 Integrins and Their Extracellular Ligands in Human Lymphoid Tissues", American Journal of Pathology, vol. 143, pp. 1098-1110 (1993).

Gretz, et al., "Lymph-borne Chemokines and Other Low Molecular Weight Molecules Reach High Endothelial Venules Via Specialized Conduits While a Functional Barrier Limits Access to the Lymphocyte Microenvironments in Lymph Node Cortex", The Journal of Experimental Medicine, vol. 192, pp. 1425-1439 (2000).

Stuart, et al., "The Human Reticular Cell: Morphology and Cytochemistry", J. Pathol, vol. 103, pp. 41-47 (1971).

Crivellato, et al., "Stromal Cell Organisation in the Mouse Lymph Node. A Light and Electron Microscopic Investigation Using the Zinc Iodide-Osmium Technique", J. Anat., vol. 190, pp. 85-92 (1997).

Gretz, et al., "Cords, Channels, Corridors and Conduits: Critical Architectural Elements Facilitating Cell Interactions in the Lymph Node Cortex", Immunological Reviews, vol. 156, pp. 11-24 (1997).

Friedl, et al., "CD4+ T Lymphocytes Migrating in Three-Dimensional Collagen Lattices Lack Focal Adhesions and Utilize Beta 1 Integrin-Independent Strategies for Polarization, Interaction with Collagen Fibers and Locomotion", Eur. J. Immunol., vol. 28, pp. 2331-2343 (1998).

Forster, et al., "CCR7 Coordinates the Primary Immune Response by Establishing Functional Microenvironments in Secondary Lymphoid Organs", Cell., vol. 99, pp. 23-33 (1999).

Gunn, et al., "Mice Lacking Expression of Secondary Lymphoid Organ Chemokine Have Defects in Lymphocyte Homing and Dentritic Cell Localization", J. Exp. Med., vol. 189, pp. 451-460 (1999).

Junt, et al., "Antiviral Immune Responses in the Absence of Organized Lymphoid T Cell Zones in plt/plt Mice", The Journal of Immunology, vol. 168, pp. 6032-6040 (2002).

Mori, et al., "Mice Lacking Expression of the Chemokines CCL21-ser and CCL19 (plt Mice) Demonstrate Delayed but Enhanced T Cell Immune Responses", J. Exp. Med., vol. 193, No. 2, pp. 207-217 (2001).

Gunzer, et al., "Antigen Presentation in Extracellular Matrix: Interactions of T Cells with Dendritic Cells are Dynamic, Short Lived, and Sequential", Immunity, vol. 13, pp. 323-332 (2000).

Miller, et al., "Two-Photon Imaging of Lymphocyte Motility and Antigen Response in Intact Lymph Node", Science, vol. 296, pp. 1869-1873 (2002).

Stoll, et al., "Dynamic Imaging of T Cell-Dendritic Cell Interactions in Lymph Nodes", Science, vol. 296, pp. 1873-1876 (2002).

Baumgarth, "A Two-Phase Model of B-Cell Activation", Immunological Review, vol. 176, pp. 171-180 (2000).

Fulcher, et al., "B-Cell Activation Versus Tolerance—The Central Role of Immunoglobulin Receptor Engagement and T-Cell Help", Int. Rev. Immunol., vol. 15, pp. 33-52 (1997).

Parker, "T Cell-Dependent B Cell Activation", Annu. Rev. Immunol., vol. 11, pp. 331-360 (1993).

Kosco-Vilbois, "Are Follicular Dendritic Cells Really Good for Nothing", Nature Reviews Immunology, vol. 3, pp. 764-769 (2003).

Skibinski, et al., "Enhancement of Terminal B Lymphocyte Differentiation in Vitro by Fibroblast-Like Stromal Cells from Human Spleen", Eur. J. Immunol., vol. 28, pp. 3940-3948 (1998).

Dubois, et al., "Dendritic Cells Enhance Growth and Differentiation of CD40-Activated B Lymphocytes", J. Exp. Med., vol. 185, pp. 941-951 (1997).

Cyster, et al., "Follicular Stromal Cells and Lymphocyte Homing to Follicles", Immunological Reviews, vol. 176, pp. 181-193 (2000).

Matsumoto, et al., "Affinity Maturation Without Germinal Centres in Lymphotoxin-α-Deficient Mice", Nature, vol. 382, pp. 462-466 (1996).

Pasparakis, et al., "Immune and Inflammatory Responses in TNFα Deficient Mice: A Critical Requirement for TNFα in the Formation of Primary B Cell Follicles, Follicular Dendritic Cell Networks and Germinal Centers, and in the Maturation of the Humoral Immune Response", J. Exp. Med., vol. 184, pp. 1397-1411 (1996).

Toyama, et al., "Memory B Cells Without Somatic Hypermutation are Generated from Bcl 6 Deficient B Cells", Immunity, vol. 17, pp. 329-339 (2002).

Galibert, et al., "CD40 and B Cell Antigen Receptor Dual Triggering of Resting B Lymphocytes Turns on a Partial Germinal Center Phenotype", J. Exp. Med., vol. 183, pp. 77-85 (1996).

Razanajaona, et al., In Vitro Triggering of Somatic Mutation in Human Naïve B Cells', The Journal of Immunology, vol. 159, pp. 3347-3353 (1997).

Phillips, et al., "Activation of Pertussis Toxin-Sensitive CXCL12 (SDF-1) Receptors Mediates Transendothelial Migration of T Lymphocytes Across Lymph Node High Endothelial Cells", Eur. J. Immunol., vol. 32, pp. 837-847 (2002).

Rot, "In Situ Binding Assay for Studying Chemokine Interactions with Endothelial Cells", Journal of Immunological Methods, vol. 273, pp. 63-71 (2003).

Irvine, et al., "Nanoscale Clustering of RGD Peptides at Surfaces Using Comb Polymers. 1. Synthesis and Characterization of Comb Thin Films", Biomacromolecules, vol. 2, pp. 85-94 (2001).

West, et al., "Polymeric Biomaterials with Degradation Sites for Proteases Involved in Cell Migration", Macromolecules, vol. 32, pp. 241-244 (1999).

Bogdan, et al., "Fibroblasts as Host Cells in Latent Leishmaniosis", J. Exp. Med., vol. 191, pp. 2121-2129 (2000).

Castro, et al., "Spleen-Derived Stromal Cells. Adhesion Molecules Expression and Lymphocyte Adhesion to Reticular Cells", Eur. J. Cell. Biol., vol. 74, 321-328 (1997).

Skibinski, et al., "The Role of Hepatocyte Growth Factor and Its Receptor c-met in Interactions Between Lymphocytes and Stromal Cells in Secondary Human Lymphoid Organs", Immunology, vol. 102, pp. 506-514 (2001).

LeBedis, et al., "Peripheral Lymph Node Stromal Cells Can Promote Growth and Tumorigenicity of Breast Carcinoma Cells Through the Release of IGF-I and EGF", Int. J. Cancer, vol. 100, pp. 2-8 (2002).

Ruco, et al., "Expression and Cell Distribution of the Intercellular Adhesion Molecule, Vascular Cell Adhesion Molecule, Endothelial Leukocyte Adhesion Molecule, and Endothelial Cell Adhesion Molecule (CD31) in Reactive Human Lymph Nodes and in Hodgkin's Disease", American Journal of Pathology, vol. 140, pp. 1337-1344 (1992).

Cyster, "Chemokines and the Homing of Dendritic Cells to the T Cell Areas of Lymphoid Organs", J. Exp. Med. vol. 189, No. 3, pp. 447-450 (1999).

Ansel, et al., "A Chemokine-Driven Positive Feedback Loop Organizes Lymphoid Follicles", Nature, vol. 406, pp. 309-314 (2000).

Mebius, "Organogenesis of Lymphoid Tissues", Nat. Rev. Immunol, vol. 3, pp. 292-303 (2003).

Poznansky, et al., "Efficient Generation of Human T Cells From a Tissue-Engineered Thymic Organoid", Nature Biotechnology, vol. 18, pp. 729-734 (2000).

Safarik, et al., "Use of Magnetic Techniques for the Isolation of Cells", Journal of Chromatography B, vol. 722, pp. 33-53 (1999).

Dynal (Norway): http://www.invitrogen.com/.

Agowa GMBH (Germany): http://agowade/contentsframes/magneticseparation/particle.html.

Chen, et al., "A Film Tension Theory of Phagocytosis", Journal of Colloid and Interface Science, vol. 190, pp. 118-133(1997).

Banchereau, et al., "Dendritic Cells and the Control of Immunity", Nature, vol. 392, pp. 245-252 (1998).

Kabashima, et al., "Prostaglandin $E_2$-EP4 Signaling Initiates Skin Immune Responses by Promoting Migration and Maturation of Langerhans Cells", Nature Medicine, vol. 9, pp. 744-749 (2003).

Denkbas, et al., "Magnetic Chotosan Microspheres: Preparation and Characterization", Reactive & Functional Polymers, vol. 50, pp. 225-232 (2002).

Larsson, et al., "Requirement of Mature Dendritic Cells for Efficient Activation of Influenza A-Specific Memory CD8 + T Cells", The Journal of Immunology, vol. 165, pp. 1182-1190 (2000).

Danke, et al., "HLA Class II-Restricted CD4+ T Cell Responses Directed Against Influenza Viral Antigens Postinfluenza Vaccination", The Journal of Immunology, vol. 171, pp. 3163-3169 (2003).

Hasbold, et al., "Quantitative Analysis of Lymphocyte Differentiation and Proliferation in Vitro Using CarboxyFluorescein Diacetate Succinimidyl Ester", Immunology and Cell Biology, vol. 77, pp. 516-522 (1999).

Luk, et al., "Rapid and Sensitive Detection of *Salmonella* (O:6,7) by Immunomagnetic Monoclonal Antibody-Based Assays", Journal of Immunological Methods, vol. 137, pp. 1-8 (1991).

Gundersen, et al., "Magnetic Bead Antigen Capture Enzyme-Linked Immunoassay in Microtitre Trays for Rapid Detection of Schistosomal Circulating Anodic Antigen", Journal of Immunological Methods, vol. 148, pp. 1-8 (1992).

Chou, et al., "The Detection of the HLA-B27 Antigen by Immunomagnetic Separation and Enzyme-Linked Immunosorbent Assay-Comparison with a Flow Cytometric Procedure", Journal of Immunological Methods, vol. 255, pp. 15-22 (2001).

Kourilov, et al., "Magnetic-Bead Enzyme-Linked Immunosorbent Assay Verifies Adsorption of Ligand and Epitope Accessibility", Analytical Biochemistry, vol. 311, pp. 166-170 (2002).

http://www.xcyte.com.

Protocol for anti-CD3 Activation of T-Cells from E-Bioscience (San Diego, CA): http://www.ebioscience..com/ebioscience/appls/AC145.htm.

Kadowaki, et al., "Subsets of Human Dendritic Cell Precursors Express Different Toll-Like Receptors and Respond to Different Microbial Antigens", J. Exp. Med. vol. 194, No. 6, pp. 863-869 (2001).

Sieben, et al., "Comparison of Different Particles and Methods for Magnetic Isolation of Circulating Tumor Cells", Journal of Magnetism and Magnetic Materials, vol. 225, pp. 175-179 (2001).

Regnier, et al., "Integration of Langerhans Cells into a Pigmented Reconstructed Human Epidermis", The Journal of Investigative Dermatology, vol. 109, No. 4, pp. 510-512 (1997).

John G. Tew et al., "*Follicular Dendritic Cells and Presentation of Antigen and Costimulatory Signals to B Cells*," Immunological Reviews (1997), vol. 156, pp. 39-52.

Akiko Furuyama et al., "*Assembly of Basement Membrane in vitro by Cooperation Between Alveolar Epithelial Cells and Pulmonary Fibroblasts*," Cell Structure and Function (1997), vol. 22, pp. 603-614.

Stephen F. Badylak et al., "*Small Intestinal Submucosa: A Substrate for in vitro Cell Growth*," J. Biomater. Sci. Polymer Edn. (1998), vol. 9, No. 8, pp. 863-878.

Shaoli Zhang et al., "*Growth Factors Secreted by Bronchial Epithelial Cells Control Myofibroblast Proliferation: An in vitro Co-culture Model of Airway Remodeling in Asthma*," Laboratory Investigation (1999), vol. 79, No. 4, pp. 395-405.

H. Garrett Thompson et al., "*A Three-dimensional in vitro Model of Angiogenesis in the Airway Mucosa*," Pulmonary Pharmacology & Therapeutics (2007), vol. 20, pp. 141-148.

M. Nakamura et al., "*Expression of Leptin in Two-layered Culture of Gastric Mucous Cells and Fibroblasts: Effect of Helicobacter pylori Attachment*," Aliment Pharmacol Ther. (2004), vol. 20, suppl. 1, pp. 125-130.

Martin N. Nakatsu et al., "*Angiogenic Sprouting and Capillary Lumen Formation Modeled by Human Umbilical Vein Endothelial Cells (HUVEC) in Fibrin Gels: The Role of Fibroblasts and Angiopoietin-1*," Microvascular Research (2003), vol. 66, pp. 102-112.

Per Brandtzaeg et al., "*Mucosal B Cells: Phenotypic Characteristics, Transcriptional, Regulation, and Homing Properties*," Immunological Reviews (2005), vol. 206, pp. 32-63.

Tarte et al., Leukemia, vol. 14, 2000, abstract p. 2182.

Kim et al., "*Three-Dimensional Tissue Culture Models In Cancer Biology*," Seminars in Cancer Biology, (2005), 15(5), pp. 365-377.

A. R. Neves, et al., "*Dendritic Cells Derived From Metastatic Cancer Vaccinated With Allogeneic Dendritic Cell-Autologous Tumor Cell Hybrids Express More CD86 and Induce Higher Levels Of Interferon-Gamma In Mixed Lymphocyte Reactions*," Cancer Immunology and Immunotherapy, (2005), 54(1), pp. 61-66.

S. Büchele et al., "*Presentation of Tetanus Toxoid To Autologous T Cells By Dendritic Cells Generated From Human Blood. Improved*

Specificity With Dendritic Cells Generated Without Fetal Calf Serum," Advances in Experimental Medicine and Biology, (1997), vol. 417, pp. 233-237.
Bai et al., "*Generation of Dendritic Cells From Human Bone Marrow Mononuclear Cells: Advantages From Clinical Applications In Comparison To Peripheral Blood Monocyte Derived Cells*," International Journal of Oncology, (2002), 20(2), pp. 247-253.
K. V. Bromelow et al., "*Whole Blood Assay For Assessment of the Mixed Lymphocyte Reaction*," Journal of Immunological Methods, (2001), 247(1-2), pp. 1-8.
M. H. Kosco et al., "*Follicular Dendritic Cells And Germinal Center Formation In-Vitro*," Accessory Cells in HIV and Other Retroviral Infections: Morphological and Functional Aspects; Workshop on Morphological and Functional Aspects of Accessory Cells in Tretroviral Infections, Hamberg, Germany, 23-24, p. 44-49 (1991).
M. H. Kosco et al., "*Folicular Dendritic Cell-Dependent B-Cell Proliferation and In Vitro Germinal Center*," Lymphatic Tissues In Vivo Immune Responses, (1991), pp. 687-690.
O. Soderberg et al., "*The Human Follicular Dendritic Cell Line FDC-1 Binds Immune Complexes And Promotes Somatic Hypermutation*," Blood, (2001), 98(11 part 2), pp. 40b.
R. Tsunoda et al., "*Human Follicular Dendritic Cells In Vitro And Follicular Dendritic-Cell-Like Cells*," Cell and Tissue Research, (1997), 288(2), pp. 381-389.
R. Tsunoda et al., "*Follicular Dendritic Cells In Vitro Modulate The Expression Of Fas and Bcl-2 on Germinal Center B Cells*," Cell and Tissue Research, (2000), 299(3), pp. 395-402.
J. G. Tew et al., "*Follicular Dendritic Cells As Accessory Cells*," Immunological Reviews, (1990), No. 117, pp. 185-211.
M. H. Kosco et al., "*Follicular Dendritic Cell-Dependent Adhesion and Proliferation Of B Cells in Vitro*," Journal of Immunology, (1992), 148(8), pp. 2331-2339.
Y. Wu et al., "*Influence Of Follicular Dendritic Cells And Primed T Cells On Somatic Hypermutation In In Vitro Germinal Centers*," Journal of Immunology, (2006), 176(suppl. S), pp. S235-S236.
M. El Shikh et al., "*Follicular Dendritic Cells Stimulated By Collagen Type I Develop Dendrites And Networks In Vitro*," Cell and Tissue Research, (2007), 329(1), pp. 81-89.
R. Seguin et al., "*Human Brain Endothelial Cells Supply Support For Monocyte Immunoregulartory Functions*," Journal of Neuroimmunology, (2003), 135(1-2), pp. 96-106.
S Levenberg et al., "*Advances In Tissue Engineering*," Current Topics In Developmental Biology, (2004), vol. 61, pp. 113-134.
P. Manna et al., "Differentiation And Functional Maturation Of Human CD14<+> Adherent Peripheral Blood Monocytes By Xenogeneic Endothelial Cells: Up-Regulation Of Costimulation Cytokine Generation, And Toll-Like Receptors," Transplantation, (2002), 74(2), pp. 243-252.
Benbrook et al., "Organotypic cultures represent tumor microenvironment for drug testing," Drug Discovery Today: Disease Models, 3(2), pp. 143-148 (2005).
International Search Report for PCT/US05/14444, dated Mar. 21, 2008.
International Search Report for PCT/US06/43563, dated Nov. 29, 2007.
International Search Report for PCT/US06/43712, dated Aug. 8, 2007.
International Search Report for PCT/US07/006532, dated Feb. 18, 2008.
International Search Report for PCT/US07/006571, dated Sep. 21, 2007.
International Search Report for PCT/US07/013871, dated Mar. 3, 2008.
International Search Report for PCT/US06/049128, dated Jun. 12, 2007.
International Search Report for PCT/US07/013745, dated Apr. 18, 2008.
H.-J. Kim et al, Establishment of Early Lymphoid Organ Infrastructure in Transplanted Tumors Mediated by Local Production of Lymphotoxin $\alpha$ and in Combined Absence of Functional B and T Cells. In J. of Immunology, vol. 172:4037-4047 (2004).
Portner, R et al, Chapter 2: An Overview on Bioreactor Design, Prototyping, and Process Control for Reproducible Three-Dimensional Tissue Culture. In Drug Testing In Vitro: Breakthrough Cell Cultur Technology. Eds. U. Marx and V. Sandig 2006: Wiley-VCH, pp. 65-69.
Okamoto et al, Artificial Lymph Nodes Induce Potent Secondary Immune Response in Naïve and Immunodeficient Mice. J. Clin. Invest. Apr. 2007, vol. 117, No. 4, pp. 997-1007.
Edelman et al, A Cultureal Renaissance: In Vitro Cell Biology Embraces Three-Dimensional Context. Exp Neurol. 2005, vol. 192, pp. 1-6.
Birkness et al., An In Vitro Tissue Culture Bilayer Model to Examine Early Events in Mycobacterium Tuberculosis Infection, *Infection and Immunity*, Feb. 1999, p. 653-658, vol. 67, No. 2.
Birkness et al., A Tissue Culture Bilayer Model To Study the Passage of Neisseria Meningitidis, *Infection and Immunity*, Feb. 1995, p. 402-409, vol. 63, No. 2.
Weppler et al., Modulation of Endotoxin-Induced Neutrophil Transendothelial Migration by Alveolar Epithelium in a Defined Bilayer Model, *Experimental Lung Research* 32:10, 455-482 (2006).
International Search Report—PCT/US2007/08379.
International Search Report—PCT/US2008/056720.
Dubois et al., J. Leukocyte Biology, 1999, v.66, p. 224-230.
Gansuvd et al., Human Immunol., 2003, v.64, p. 427-439.
Clayton et al., Clin. Exp. Immunol., 2003, v.132, p. 174-179.
D'Amico et al., Blood 92:207-214 (1998).
Simmingskoeld et al., Scand. J. Immunol. 7:233-238 (1978).
Transwell® Permeable Supports Selection and Use Guide, Corning Corp., pp. 1-12 (2009).
Khademhosseini et al., "Microscale Technologies for Tissue Engineering and Biology," Proc. Natl. Acad. Sci. USA, vol. 103, pp. 2480-2487 (2006).

\* cited by examiner

DISEASE MODEL INCORPORATION INTO AN ARTIFICIAL IMMUNE SYSTEM (AIS)

CROSS-REFERENCE TO RELATED APPLICATIONS

This application is a continuation-in-part of U.S. application Ser. No. 11/453,003, filed Jun. 15, 2006, now issued as U.S. Pat. No. 7,709,256, which was a continuation-in-part of U.S. application Ser. No. 11/116,234, filed Apr. 28, 2005, which claims the benefit of priority of both U.S. Provisional Application Serial No. 60/565,846, filed Apr. 28, 2004, and U.S. Provisional Application Serial No. 60/643,175, filed Jan. 13, 2005. Each of these applications is hereby incorporated by reference in its entirety.

FIELD OF THE INVENTION

The present invention is directed to a method for developing a disease model that may be used with an artificial human immune system for in vitro testing of vaccines, adjuvants, immunotherapy candidates, cosmetics, drugs, biologics, and other chemicals. The disease model and artificial immune system of the present invention is useful for assessing disease pathogenesis and the effect of vaccines, drugs, biologics, immunotherapeutics, and adjuvants on a disease. In the context of vaccines, for example, the disease models and artificial immune system of the present invention could be used to predict the effectiveness of a vaccine by means of an in vitro challenge with disease agents. The disease models and artificial immune systems of the present invention can be prepared using cells from healthy (not diseased, uninfected, naïve) individuals or from individuals suffering from diseases or infections. "Diseased cells" include virally infected cells, bacterially infected cells, and tumor cells, and cells and tissues affected by a pathogen or involved in an immune-mediated disease, such as, e.g., autoimmune disease. Embodiments of the present invention can be used to accelerate and improve the accuracy and predictability of vaccine and drug development.

BACKGROUND OF THE TECHNOLOGY

The development and biological testing of human drugs and vaccines has traditionally relied on small animal models (e.g., mouse and rabbit models) in the early stages and then on larger animals, such as dogs and non-human primates, in later stages. However, animal models of disease are often only approximations of the human disease state, and in some cases animal models are not available at all (e.g., pathogens that infect only humans). Thus, animal models of disease may not accurately predict outcomes in human studies or may not be available to make such predictions.

In the case of diseases that involve human immunology, such as an immune response to a pathogen or a deleterious inflammatory response, like psoriasis, a major problem remains the translation from animal test systems to human immunology. Successful transfer between traditional testing systems and human biology requires an intricate understanding of disease pathogenesis and immunological responses at all levels. Thus, there is a need for a system that uses human immune cells to simulate human immune responses in the context of a disease state.

DESCRIPTION OF THE INVENTION

The present invention comprises the use of an artificial immune system (AIS) with disease models to provide essentially the ability to conduct a "clinical trial in a test tube" to predict the efficacy of a vaccine, adjuvant, drug, or other agent on a disease that involves the immune system (e.g., pathogen response, autoimmune disease, cancer response). FIG. 1 illustrates schematically an example of the integration of the AIS and a disease model. As an example, schematically, the VS is where infection or vaccination occurs, the LTE is where immune induction occurs, and the disease model is where the immune response to the disease occurs.

Models of the present invention are particularly appropriate for examining diseases and infections that involve immune system cells. Examples include HIV, tuberculosis, tularemia, filoviruses, *Yersinia*, and *Burkholderia*. The in vitro disease models of the present invention can also be used to understand basic disease pathogenesis. The artificial immune system of the present invention comprises three modules: the first simulates the innate immune response (the vaccination site, VS, module), the second simulates the adaptive immune response for the detection of T and B cell responses in vitro, providing a model for the interaction of immune cells within lymph nodes (the lymphoid tissue equivalent, LTE, module); and the third module is a functional assay or disease module that uses the products of the other two modules together with, for example, a pathogen or human tissue, to measure the effect of the immune response to a disease, such as influenza, glanders, tularemia, tuberculosis, Ebola, Marburg, plague, or AIDS, directly rather than through the use of surrogate markers. These artificial immune system modules reproduce the conditions that exist in the human body, such as the spatial segregation of different immune cells and temporal dynamics that bring different immune cells together at different times. Other variations are possible, such as using the LTE for both immune induction and the immune response, so that the LTE effectively becomes a disease model.

The disease models and artificial immune systems of the present invention can be prepared using cells from healthy (not diseased, uninfected, naïve) individuals or from individuals suffering from diseases or infections. "Diseased cells" include pathogen-infected cells, e.g., virally infected cells and bacterially infected cells, tumor cells, and cells and tissues affected by a pathogen or involved in an immune-mediated disease, such as, e.g., autoimmune disease.

As examples, disease models of the present invention include viral (e.g., herpes simplex virus, hepatitis A, B, C, VSV, HIV, vaccinia virus, influenza virus), tumoral (e.g., melanoma), and autoimmune models (e.g., RA, diabetes, psoriasis, Crohn's disease).

A primary goal of a preclinical testing program is to improve outcome for patients by the early identification of potential applications for new vaccine or drug agents before clinical development. The premise for establishing an in vitro testing effort is that it will allow candidates to be selected for clinical evaluation with increased likelihood for clinical benefit. Clearly, this requires that the in vitro system be predictive of human responses to the vaccine or drug and the efficacy of the vaccine or drug against the disease in question. In the absence of an effective and predictive preclinical testing program, ineffective vaccines and drugs are likely to be selected for evaluation, thus slowing progress in improving outcomes. Furthermore, having an in vitro testing system that is predictive (a "clinical trial in a test tube") will significantly reduce lost opportunity costs associated with vaccine or drug testing. That is, if a candidate is going to fail, it should fail early.

The development of an artificial immune system coupled with a disease model has the potential to change the way vaccines and drugs are tested. The preclinical in vitro testing program of the present invention, though based on both immunologic and engineering principles, has the very pragmatic objective of providing reliable, predictive, and reproducible information to clinical investigators to allow enlightened prioritization among the multiple candidates available. Clearly, that is a goal of all preclinical testing, but what is new in the in vitro testing system of the present invention is an in vitro model using functionally equivalent tissue engineered constructs populated with human cells. In comparison with in vivo animal testing, in vitro testing using the system comprising the present invention is less expensive, less time-consuming, and importantly more predictive of clinical outcomes.

The present invention concerns the development of accurate, predictive in vitro models to accelerate vaccine testing, allowing collection of more informative data that will aid in redesigning and optimizing vaccine and drug formulations before animal or clinical trials, and raise the probability that a vaccine or drug candidate will be successful in human trials.

More specifically, the present invention comprises controlling the nature and state of the cells in the lymphoid tissue equivalent (LTE, artificial lymph node) of the artificial immune system (AIS). The AIS can be used to test vaccines and other pharmaceuticals for immune reactivity in a manner that is more predictive than animal experiments. Consequently, it can provide valuable pre-clinical data earlier in the research and development process. Antigenic molecules introduced to the AIS are acquired by dendritic cells (DCs) at the vaccination site (VS). The DCs are then transferred to the lymphoid tissue equivalent (LTE), where they present the antigen to T cells, activating their immune function. Activated helper T cells co-stimulate B cells to induce antibody production, while activated cytotoxic T cells lyse antigen-bearing cells. Solubilized antigen(s) can also be introduced into the LTE to directly activate B cells for subsequent antibody production. In other embodiments, pathogens, not antigenic molecules, are introduced to the AIS and infect APCs, e.g., dendritic cells (DCs), at the vaccination site (VS). In other embodiments, pathogens are introduced to the AIS and infect cells in the LTE.

While a number of published reports have demonstrated antigen-specific B cell responses (to *C. albicans*, TT, and other antigens) in vitro, these results are typically achieved by stimulating and restimulating cultures of whole PBMCs with antigen and exogenous factors to boost B cell proliferation and/or activation. Embodiments of the present invention comprise the detection of immune responses using defined cultures of B cells, T cells, and DCs and optionally follicular dendritic cells (FDCs), in 2-dimensional construct assays. The presence of secondary cells provides a more physiological environment for B cell activation and differentiation, such that artificial factors in the cultures are not necessary to detect specific immune responses.

Using embodiments of the present invention, we have generated antigen-specific B cell responses using a (2D) co-culture system comprising T cells, B cells, and antigen-pulsed DCs. Responses have been generated against tetanus toxoid (TT) and a whole protein extract of *Candida albicans* (*C. albicans*) influenza, recombinant protective antigen of *Bacillus anthracis*, hepatitis B, yellow fever, rabies and merozoite surface protein 1 (MSP-1) from malaria. These results show that culturing human T and B cells together in vitro at, for example, a ~1:1 ratio, versus the ratio of T and B cells naturally found in the blood, gave stronger antigen responses, by both analysis of activation and proliferation (flow cytometry) and antibody production (ELISPOT), Here, "T cells" includes both $CD4^+$ and $CD8^+$ T cells. In peripheral blood, the T (total T cells):B ratio is ~7:1. In the lymph node, the T (total T cells):B ratio is ~1:1.6. In the germinal center, the T:B ratio is ~1:8, and there, the T cells are primarily $CD4^+$ T cells.

It is known that 3-dimensional biology is important to induce proper functionality of immunological engineered tissue constructs (ETCs; see, e.g., Edelman & Keefer, *Exp. Neurol.* 192:1-6 (2005)). A principal approach to studying cellular processes is to culture cells in vitro. Historically, this has involved plating cells on plastic or glass supports. Cells grown on solid or filter support are referred as two-dimensional (2D) cultures. Such 2D cultures on porous supports have been useful in studying many aspects of biology. However, more in vivo-like conditions can now be realized in 3D cultures.

In lymph nodes, it has been shown that 3D interstitial tissue matrix facilitates not only T cell migration toward an APC, but also supports motility upon cell-cell interaction. A 3D collagen matrix environment, because of its spatial architecture, provides traction for lymphocyte crawling, mimicking some structural features of the lymph node cortex. This provides experimental justification for the importance of a 3D environment in the constructs that comprise some embodiments of the artificial immune system of the present invention.

The present invention also differs significantly from existing in vitro disease models. For example, simple monolayer and suspension cultures are commonly used to model viral infection and tumors. However, such cell cultures provide a highly artificial cellular environment and are not coupled to an artificial immune system.

The disease models of the present invention include cancer models. Although historically mice have been used for studying tumor genetics, physiology, and therapeutic regimens, murine tissue models have many limitations. An important difference is that human tumors are primarily epithelial in origin, whereas murine tumors are typically non-epithelial (such as sarcomas, lymphomas). Many agents that are carcinogenic in mice are not in humans, and vice versa. Oncogenic pathways are different in many ways in the mouse compared to humans. Additionally, the murine basal metabolic rate is six times higher than in humans. New approaches have examined xenograft placement on immune-deficient mice with more success; however, the murine component still exists in this model. (Ortiz-Urda et al. (2002) *Nature Med* 8, 1166-70). Thus, studying human tumor models in a human cell-based model of the present invention removes these interspecies differences.

Recent work by Mertsching and colleagues at the Fraunhofer Institute of Interfacial Engineering and Biotechnology, Germany, is beginning to demonstrate that in vitro 3D models can be a useful platform in cancer research. They developed a new, 3D, vascularized tissue construct. The vascularized 3D matrix is populated with endothelial cells and then with tumor cells to create an ex vivo vascularized tumor-like structure as a disease model. Their data suggests that this in vitro model offers the possibility to simulate physiological drug application and provide a human 3D test system for cancer research/therapy.

In the present invention, such a 3D tumor model could be used in conjunction with an artificial immune system to predict the effectiveness of a cancer vaccine on a tumor rather than on isolated cancer cells in a 2D culture. This distinction is important. Antibodies and immune effector cells must reach the tumor in sufficient numbers to have an impact on the disease. Access to the cancer cells is not an issue with cell cultures, but can become a problem with a vascularized tumor. In addition, tumors may induce surrounding tissues to secrete factors that induce immune tolerance, thus counteracting the immune enhancement induced by a cancer vaccine. These types of effects may not be observed in the absence of a tumor disease model that interacts with an artificial immune system.

The disease models of the present invention include pathogen infection models (e.g., viral, bacterial, fungal, protozoan, parasitic). In embodiments of the present invention, we use cells in 2D culture. In other embodiments, we use cells placed with a 3D tissue-engineered construct. The infected or diseased cells can be included in the engineered tissue construct. For example, virally infected epithelial cells can be used in a tissue engineered skin or mucosal equivalent. As another example, herpes simplex viruses are ectodermotropic (i.e., they can infect and reproduce in epithelial cells and reside in neurons in a latent state). The disease model in this case could use virally infected epithelial cells or neurons, or both, to model both active and latent herpes virus infection. In other embodiments of the present invention, we use engineered tissue constructs to model viral transport and infection in compartments that are separated from the primary infection site.

For example, HIV-1 is captured by dendritic cells (DCs) and delivered to the lymph node, where the virus is then transmitted to CD4$^+$ T cells. The lymph node then becomes the principal site of virus production. In an embodiment of the present invention, the vaccination site (VS) module would be the infection site, where HIV infects the APCs, e.g., DCs, which would then be placed into the lymphoid tissue equivalent module, where the infected DCs transmit the virus to CD4$^+$ T cells. In this case, the LTE would serve as the disease module. Collectively, the infection site and disease module would comprise the disease model.

The disease models of the present invention include inflammatory and autoimmune diseases. In these diseases (e.g., psoriasis, rheumatoid arthritis), the immune system itself is primarily responsible for the disease state. In one embodiment of the present invention, an LTE could be constructed from immune cells isolated from the blood of donors afflicted with psoriasis. An engineered tissue construct could be made from biopsied skin from the same donor. The interaction of the AIS and the disease model under different conditions could yield insight into disease pathogenesis. Also, one could test different candidate drugs for psoriasis in this disease model to determine potential efficacy of a candidate. If this process was repeated for a large number of donors afflicted with psoriasis, the resulting "clinical trial in a test tube" could facilitate the selection of an optimal clinical candidate for the largest number of patients or the selection of several candidates, which are targeted at different patient populations through the use of clinically relevant biomarkers. In another embodiment of the present invention, the disease model would simulate an aspect of an autoimmune or inflammatory disease, rather than the disease itself. For example, an important hallmark of certain inflammatory diseases is the migration of neutrophils to the site of inflammation. If this process of neutrophil migration could be interrupted, then the inflammatory process could be interrupted, with a corresponding beneficial effect on the disease state. The AIS could, thus, be used to model neutrophil migration as a proxy for modeling the resulting inflammatory disease.

HIV models. HIV (human immunodeficiency virus) is the virus that causes AIDS (acquired immune deficiency syndrome). An embodiment of the present invention comprises a HIV disease model. In vivo, HIV-1 infects DCs and they move to the lymph nodes where the virus infects CD4$^+$ T cells. The lymph node then becomes the principal site of virus production.

Infection with HIV-1 is associated with a progressive decrease in the CD4$^+$ T cell count and an increase in viral load. The stage of infection can be determined by measuring the patient's CD4$^+$ T cell count, and the level of HIV in the blood. This acute viremia is associated in virtually all patients with the activation of CD8$^+$ T cells, which kill HIV-infected cells, and subsequently with antibody production, or seroconversion. The CD8$^+$ T cell response is thought to be important in controlling virus levels, which peak and then decline, as the CD4$^+$ T cell counts rebound to ~800 cells/mL (normal is ~1200 cells/mL). A strong CD8$^+$ T cell response has been linked to slower disease progression and a better prognosis, though it does not eliminate the virus. During this early phase of infection, HIV is active within lymphoid organs, where large amounts of virus become trapped in the follicular dendritic cells (FDC) network. The surrounding tissues that are rich in CD4$^+$ T cells may also become infected, and viral particles accumulate both in infected cells and as free virus.

Tularemia models. *Francisella tularensis* is a Category A biowarfare agent and is an important focus of biodefense research. An embodiment of the present invention comprises a tularemia disease model. The pathogenicity of *F. tularensis* is quite similar to that of *Mycobacterium tuberculosis* (Mtb), in that both infect macrophages and dendritic cells (Clemens et al. (2004) Infect. Immun. 72, 3204-17). *F. tularensis* is a Gram-negative bacterium responsible for tularemia, a zoonotic disease that affects many mammals and is occasionally transmitted to humans through tick bites, by direct contact with an infected animal, or through aerosolization of contaminated materials. The progression and the severity of the disease depend on the host immune status and on the infecting strain. There are four known subspecies of *F. tularensis* (*tularensis, holarctica, mediasatica, novicida*); *tularensis* is the most virulent. The live vaccine strain (LVS) was derived from the *holarctica* subspecies and is widely used to study tularaemia. The subspecies *novicida* is less virulent in humans.

*F. tularensis* infects macrophages, dendritic cells, hepatocytes and alveolar epithelial cells. Its virulence depends on its ability to multiply inside host cells. Upon entering the host cell, *F. tularensis* is taken up into a phagosome. It prevents acidification and maturation of the phagosome (Clemens et al. (2004) Infect. Immun. 72, 3204-17), escapes the phagosome, and multiplies in the cytosolic compartment of the host cells. This replication is dependent on a cluster of genes known as the *Francisella* pathogenicity island (FPI). Upon escaping into the cytosol, *F. tularensis* activates many pathways of the innate immune system, including the inflammasome, which triggers both a caspase-1-mediated apoptotic cascade in the host cell and also a pro-inflammatory cytokine response (Henry & Monack (2007) Cell. Microbiol. 9, 2543-255). Cytokines including IL-18, IL-1b, IFN-γ, IL-12, and the Th2 cytokines IL-4 and IL-5, are known to play important roles in the immune response against *F. tularensis* (Henry & Monack (2007) Cell. Microbiol. 9, 2543-255).

Although the role of antibodies in protection against respiratory infection with *F. tularensis* is unclear, one study reported prophylactic and therapeutic use of antibodies for protection against respiratory infection (Kirimanjeswara et al. (2007) J. Immunol. 179, 532-9). Serum antibodies (immune serum from infected mice) were capable of conferring complete protection against lethal respiratory tularemia to a naïve mice when given 24-48 h post-exposure.

Filovirus models. The filoviruses Marburg and Ebola are Category A biowarfare agents. An embodiment of the present invention comprises a filovirus disease model. Filoviruses are enveloped, non-segmented, negative-stranded RNA viruses.

The virions contain a 19 kb non-infectious genome that encodes seven structural proteins, with a gene order of: 3' leader, nucleoprotein (NP), virion protein (VP) 35 (VP35), VP40, glycoprotein (GP), VP30, VP24, polymerase L protein, and 5' trailer (Sanchez et al. (199) Virus Res. 29, 215-240). Studies using reconstituted replication systems showed that transcription/replication of Marburg virus requires three of the four proteins (NP, VP35, L), while transcription/replication of Ebola virus requires all four proteins (Muhlberger et al. (1999) J. Virol. 73, 2333-2342). GP is the surface glycoprotein of the virion and is important for receptor binding and membrane fusion (Takada et al. (1997) Proc. Natl. Acad. Sci. USA 94, 14764-69; Ito et al. (1999) J. Virol. 73, 8907-8912).

Most research to date on filovirus infections has come from experimental infection of non-human primates, including cynomolgus macaques and African green monkeys. Rodent models of filovirus infection have provided data on the efficacy of candidate drugs and vaccines, but do not faithfully reproduce the viral pathogenesis and immunity in humans (Bray et al. (2001) J. Comp. Pathol. 125, 243-253; Geisbert et al. (2002) Emerg. Infect. Dis. 8, 503-507). Indeed, there is currently only limited data available on the pathophysiology of filovirus infections in humans.

Both Ebola and Marburg viruses have broad cell tropisms and use a variety of host cell surface molecules to gain entry into host cells. Infection of monocytes/macrophages and dendritic cells is central to the pathology of Ebola virus infection (Stroher et al. (2001) J. Virol. 75, 11025-33), triggering a cascade of events leading to the production and release of the procoagulant protein tissue factor (TF) (Geisbert et al. (2003a) J. Infect. Dis. 188, 1618-1629) and a variety of cytokines/chemokines (Stroher et al. (2001) J. Virol. 75, 11025-33; Hensley et al. (2002) Immunol. Lett, 2002, 80, 169-179). Although lymphocytes are not infected by Ebola or Marburg viruses, there is large-scale destruction of these cells, said to be the result of "bystander" apoptosis (Geisbert et al. (2000) Lab. Invest. 80, 171-86). Reasons for this aberrant apoptosis of lymphocytes are unclear. An embodiment of the present invention comprises an in vitro disease model that can be used to explore this phenomenon.

It has been suggested that infection of monocytes/macrophages, damage to endothelial cells, and release of procoagulant protein tissue factor appear to be the cause for the development of hemorrhage, shock, and coagulation defects such as disseminated intravascular coagulation (DIC) during filoviral infections (Geisbert et al. (2003a) J. Infect. Dis. 188, 1618-1629).

In studies involving infection of non-human primates with Ebola virus, increased circulating levels of IFN α, IL-6, MCP-1, MIP-1a, MIP-1b, IFN-β, IFN-γ, IL-18, and TNF-α at different stages of disease were observed (Geisbert et al. (2003b) Am. J. Pathol. 163, 2347-2370). In human cases, an association between increased levels of IL-10 and increased fatalities was observed in Ebola virus infection (Baize et al. (2002) Clin. Exp. Immunol. 128, 163-168). Other in vitro studies with different types of primary human cells showed similar increases in proinflammatory cytokine levels (Stroher et al. (2001) J. Virol. 75, 11025-33; Hensley 2002) and also that results varied due to human donor-associated genetic differences. In using the VS module to model filovirus disease, cytokine production in the VS module is monitored as are phenotypic changes in the APCs.

Early attempts to develop filoviral vaccines have used cell culture-propagated filoviruses inactivated with formalin or heat-treatment, but the protection offered was inadequate (Geisbert et al. (2002) Emerg. Infect. Dis. 8, 503-507). Current efforts use different recombinant vectors, such as VSV and adenoviral vectors, for expression of filoviral-encoded proteins individually or in combinations (Geisbert & Jahrling (2003c) Exp. Rev. Vaccines 2, 777-789). GP and NP are being tested as vaccine candidates in non-human primates with encouraging results (Sullivan et al. (2003) Nature 424, 681-4). There are currently no effective post-exposure treatments for filoviral infections.

*Yersinia* models. The genus *Yersinia* includes three species that are pathogenic to humans, *Y. enterocolitica*, *Y. pestis*, and *Y. pseudotuberculosis* (Brubaker (1991) Clin. Microbiol. Rev. 4, 309-324). An embodiment of the present invention comprises a *Yersinia* disease model. *Y. pestis*, a Gram-negative bacterium, is the agent of plague, a lethal disease transmitted by flea bites or by aerosols (Perry & Fetherston (1997) Clin. Microbiol. Rev. 10, 35-66). *Y. pestis* has been the cause of three pandemics (Drancourt et al. (2004) Emerg. Infect. Dis. 10, 1585-92), and has resulted in the deaths of millions of people.

*Y. pseudotuberculosis* and *Y. pestis* are closely related. It is believed that *Y. pestis* may have evolved from *Y. pseudotuberculosis* (Skurnik et al. (2000) Mol. Microbiol. 37, 316-330; Achtman et al. (1999) Proc. Natl. Acad. Sci. USA 96, 14043-48). Minor phenotypic differences have been used to classify *Y. pestis* strains into three biovars (Antiqua, Mediaevalis, Orientalis) (Perry & Fetherston (1997) Clin. Microbiol. Rev. 10, 35-66). Despite differences in their mode of entry into the host and severity of disease, all three pathogenic *Yersinia* species exhibit a common tropism for lymphoid tissue (Brubaker (1991) Clin. Microbiol. Rev. 4, 309-324). The complete genome sequence of *Y. pestis* has been determined (Parkhill et al. (2001) Nature 413, 523-527; Deng W et al. (2002) J. Bacteriol. 184, 4601-4611).

In the pathogenic *Yersinia* spp., several virulence factors have been identified that promote serum resistance and the acquisition of iron (Brubaker (1991) Clin. Microbiol. Rev. 4, 309-324; Perry & Fetherston (1997) Clin. Microbiol. Rev. 10, 35-66; Carniel 2002). Additionally, they contain a 70-kb plasmid that is necessary for sustained bacterial replication in host tissues (Cornelis et al. (1998) Microbiol. Mol. Biol. Rev. 62, 1315-1352). A type III secretion system (TTSS) and several secretion substrates (Yops, LcrV) are expressed from the virulence plasmid when *Yersinia* spp. are grown at 37° C. (Cornelis et al. (1998) Microbiol. Mol. Biol. Rev. 62, 1315-1352; Perry & Fetherston (1997) Clin. Microbiol. Rev. 10, 35-66). After they are secreted by the TTSS, the Yops are delivered into the phagocytes, where they inhibit phagocytosis and proinflammatory cytokine production and also trigger apoptosis of host cells (Cornelis (2002) J. Cell. Biol. 158, 401-408). LcrV is secreted into the extracellular milieu where it inhibits inflammation by interacting with Toll-like receptor 2 (Brubaker (2003) Infect. Immun. 71, 3673-3681). *Y. pestis* carries two plasmids, pMT1 and pPCP1, that impart *Y. pestis* with increased virulence (pMT1 and pPCP1) and vector-borne transmissibility (pMT1) (Carniel (2002) Curr. Top. Microbiol. Immunol. 264, 89-108; Perry & Fetherston (1997) Clin. Microbiol. Rev. 10, 35-66).

*Y. pestis* causes *bubonic* plague when its mode of entry is intradermal following the bite from an infected flea, while it causes pneumonic plague when infection is by inhalation of infectious droplets (Brubaker (1991) Clin. Microbiol. Rev. 4, 309-324; Perry & Fetherston (1997) Clin. Microbiol. Rev. 10, 35-66). Disease pathogenesis has been studied in mice and non-human primates (Welkos et al. (1997) Microb. Pathogen. 23, 211-223; Finegold (1969) Am. J. Pathol. 54, 167-185). Bacteria multiply at the initial site of infection before entering the lymphatic system and spread to regional lymph nodes and via the bloodstream to other organs, such as spleen and liver.

Macrophages may act as the vehicle for transport from the initial site of infection to the lymphoid tissues. Extensive bacterial replication in visceral organs leads to septicemia and death of the host (Brubaker (1991) Clin. Microbiol. Rev. 4, 309-324; Perry & Fetherston (1997) Clin. Microbiol. Rev. 10, 35-66). Animal studies have indicated that in the later stages of infection process (more than 12 h post-infection) Y pestis was found to replicate in necrotic foci extracellularly (Welkos et al. (1997) Microb. Pathogen. 23, 211-223; Nakajima et al. (1995) Infect. Immun. 63, 3021-3029).

*Y. pestis* has long been considered a facultative intracellular pathogen (Cavanaugh & Randall (1959) J. Immunol. 85, 348-363). Animal studies have indicated that *Y. pestis* can survive and replicate within macrophages (Finegold 1969), but is killed intracellularly by neutrophils (Cavanaugh & Randall (1959) J. Immunol. 85, 348-363; Burrows & Bacon (1956) Br. J. Exp. Pathol. 37, 481-493). Thus, macrophages effectively serve as permissive sites for replication in the early stages of infection. *Y. pestis* achieves this by subverting the normal antibacterial functions of macrophages. A study in inbred and outbred strains of mice infected with pneumonic plague showed that proinflammatory cytokines, such as like IL-6, TNFα, IFNγ, IL-12, and MCP-1 are found in the bronchioalveolar lavage fluids in later stages of infection (Bubeck et al. (2007) Infect. Immun. 75, 697-705). In the host immune response to plague, *Y. pestis*-infected human monocytes were reported to express TLR9 and differentiate into dendritic cells (Saikh et al. (2004) J. Immunol. 173, 7426-34). *Y. pestis* is known to evade immune responses in part by injecting host immune cells with several effector proteins called Yersinia outer proteins (Yops) that impair cellular function. *Y. pestis* YopJ disrupts signal transduction pathways and interferes with DC differentiation and subsequent function (Lindner et al. (2007) Eur. J. Immunol. 37, 2450-62). Further, YopJ injection prevents upregulation of costimulatory ligands, and LPS-induced cytokine expression in DC thus crippling the adaptive response via a diminished capacity to induce T cell proliferation and IFNγ induction.

An effective vaccine should induce both humoral and cellular immune responses that contribute to protection (Zinkemagel (2003) Annu. Rev. Immunol. 21, 515-546). Humoral immunity involves antibody production by B cells that act to neutralize an extracellular pathogen, its proteins, and toxins, while cellular immunity involves production of cytokines and cytolytic capacities of T cells and acts to eradicate intracellular pathogens. Vaccines composed of either killed pathogen or purified proteins mixed with adjuvants act by priming humoral immunity (Meyer et al. (1974) J. Infect. Dis. 129 (Suppl.), S13-S18; Heath et al. (1998) Vaccine 16, 1131-1137). In contrast, live attenuated vaccines of virulent pathogens, act by priming cellular immunity (Levine & Sztein (2004) Nat. Immunol. 5, 460-464). The importance of cellular immunity in providing vaccine protection against *Y. pestis* has been demonstrated using a mouse model (Parent et al. (2005) Infect. Immun. 73, 7304-10). This report shows the importance of CD4 and CD8 T cells in immunity to *Y. pestis* and that IFNγ and TNFα secreted by these cells played an important role in it.

Early plague vaccine research centered on the bubonic form of disease. Heat-killed cultures of virulent *Y. pestis* formulated as vaccine were used by Haffkine in 1897 (Haffkine (1897) Br. Med. J. 1, 1461). Kolle & Otto found that live attenuated *Y. pestis* strains protected mice against virulent infection (Kolle & Otto (1904) Z. F. Hyg. 48, 399-428). Though these live attenuated strains were used in humans and their safety and efficacy was established (Strong (1908) J. Med. Res. 18, 325-346), they occasionally caused adverse reactions. Pneumonic plague vaccine efforts have largely focused on the development of subunit vaccines using recombinant *Y. pestis* proteins (Titball & Williamson (2004) Expert Opin. Biol. Ther. 4, 965-973); fraction 1 (F1) and V have been widely tested in vaccinations and these recombinant proteins protects mice against pneumonic plague (Williamson et al. (1995) FEMS Immunol. Med. Microbiol. 12, 223-230; Anderson et al. (1996) Infect. Immun. 64, 4580-4585; Andrews et al. (1996) Infect. Immun. 64, 2180-2187). A recombinant F1-V fusion protein vaccine has been reported to protect mice (Heath et al. (1998) Vaccine 16, 1131-1137), but does not fully protect non-human primates against pneumonic plague.

The current treatment regimen for plague comprises use of the antibiotics tetracycline, streptomycin, and chloramphenicol. Recently gentamicin, chloramphenicol, doxycycline and ciprofloxacin have also been recommended.

Burkholderia models. *Burkholderia mallei*, is a category B biowarfare agent per the CDC classification. *B. mallei* is a Gram-negative, non-motile *bacillus*, and causes glanders primarily in horses, mules, and donkeys. An embodiment of the present invention comprises a *burkholderia* disease model. It infects by the oral route and spread is by close contact with infected animals. Infection of horses is most often manifested as a slow progressive, chronic disease, whereas in donkeys, the disease is usually severe, causing death in 7-10 days (Acha & Szyfres (1987) Zoonoses and communicable diseases common to man and animals. 2nd ed. Washington, D.C.: World Health Organization). Other animals such as mice, hamsters, guinea pigs, monkeys, and dogs, are also susceptible to this pathogen (DeShazer 2004). *B. mallei* can also infect by the cutaneous route. There is no effective treatment for glanders in the natural host, and animals diagnosed with glanders are typically isolated and destroyed. In humans, infection with *B. mallei* can occur via mucosal (oral, nasal, ocular) or cutaneous routes. Currently, there is no vaccine against *B. mallei*. Because of its potential use as a biowarfare agent, a vaccine against *B. mallei* is a high priority. Indeed, *B. mallei* was used as a bioweapon in the First World War by German troops to disable the Russian army's horses and mules (Aldhous (2005) Nature 434, 692-3).

A genetically related species, *Burkholderia pseudomallei*, causes melioidosis which has a fatality rate of almost 50% in countries such as Thailand (Aldhous (2005) Nature 434, 692-3). It is endemic in parts of Asia and in northern Australia. *B. pseudomallei* is also considered a potiential bioterrorism agent. Another species, *Burkholderia thailandensis*, is considered non-pathogenic in humans.

The complete genome sequence of *B. pseudomallei* (Holden et al. (2004) Proc. Natl. Acad. Sci. USA 101, 14240-14245) has been determined by the Wellcome Trust, UK, and that of *B. mallei* (Nierman et al. (2004) Proc. Natl. Acad. Sci. USA 101, 14246-51) was determined by TIGR. It appears that *B. mallei* evolved from *B. pseudomallei* by deletion of portions of its genome (Godoy et al. (2003) J. Clin. Microbiol. 41, 2068-2079). There are reports that gene losses have contributed to the pathogenic evolution of bacterial species (Maurelli et al. (1998) Proc. Natl. Acad. Sci. USA 95, 3943-3948; Moore et al. (2004) Infect. Immun. 72, 4172-87). The non-pathogenic *B. thailandensis* has the ability to assimilate arabinose using proteins encoded by an arabinose assimilation operon, while the pathogenic species *B. mallei* and *B. pseudomallei* have lost this operon. Thus, genes for arabinose assimilation have been termed anti-virulence genes (Moore et al. (2004) Infect. Immun. 72, 4172-87).

Analysis of the genome sequence of *B. pseudomallei* identified several genes encoding survival and virulence functions, including three type III secretion system (TTSS) genes, while in *B. mallei* genes responsible for the virulence function form a gene cluster encoding an exopolysaccharide capsule (DeShazer et al. (2001) Microb. Pathogen. 30, 253-269) and a TTSS (Ulrich & DeShazer (2004) Infect. Immun. 72, 1150-1154). The TTSS was found to be essential for intracellular survival of *Burkholderia mallei* within human macrophage-like cells (Ribot & Ulrich (2006) Infect. Immun. 74, 4349-53).

Several animal species have been used a models of human *B. mallei* infection, including monkeys, guinea pigs, hamsters, and mice. Acute glanders in humans is characterized by rapid onset of pneumonia; as a result, an aerosol model of infection in Balb/c mice was developed (Lever et al. (2003) J. Med. Microbiol. 52, 1109-15). In the initial stage of the disease, the pathogen localizes in the upper and lower sections of the respiratory tract and is transported by alveolar macrophages to regional lymph nodes. As disease progresses, bacteria disseminate and are also found in other organs, including liver and spleen, and in the bloodstream in later stages.

In the host immune response to *B. mallei* infection, type I cytokines, IFNγ and IL-12, are key in controlling the initial infection (Rowland et al. (2006) Infect. Immun. 74, 5333-40). In that report, increased levels of IFNγ, IL-6, MCP-1, IL-12p35, IL-18, and IL-27 were found in the serum and spleen of peritoneally-infected mice. IFNγ knockout mice were unable to control infection and died within 2-3 days, suggesting the importance of IFNγ in host immunity to *B. mallei* infection. *B. mallei* has an outer lipopolysaccharide (LPS) capsule. It has been reported that *B. mallei* LPS is a potent activator of human Toll-like receptor (TLR) 4 (Brett et al. (2007) Mol. Microbiol. 63, 379-90), eliciting TLR4-mediated stimulation of human macrophage-like cells (THP-1, U-937), monocyte-derived macrophages, and dendritic cells, resulting in high levels of TNF-α, IL-6, and RANTES. These observations suggest that the *B. mallei* LPS capsule plays an important role in the pathogenesis of the human disease.

As *B. mallei* and *B. pseudomallei* are naturally soil-dwelling microbes, they are intrinsically resistant to many antibiotics. In a study on 65 isolates of *B. mallei* and *B. pseudomallei*, a wide range of resistance to antimicrobial agents was noted, including to fluoroquinolones, β-lactam antibiotics, aminoglycosides, and macrolides. Bacteria were found to be susceptible to imipenem, ceftazidime, piperacillin, piperacillin/tazobactam, doxycycline, and minocycline (Thibault et al. (2004) J. Antimicrob. Chemother. 54, 1134-8). These antibiotics are currently being used in post-exposure treatment of melioidosis and glanders.

A report indicated that pretreatment of Balb/c mice with an oligodeoxynucleotide (ODN) containing CpG motifs (CpG ODN 7909) protected them against aerosol challenge with *B. mallei*. This protection was found to be associated with enhanced levels of interferon gamma (IFNγ)-inducible protein 10 (IP-10), IL-12, IFNγ, and IL-6. Thus, treatment with CpG ODN 7909 provided an effective pre-exposure therapy to protect against glanders. CpG ODN 7909 is an agonist of TLR9. TLRs 7 and 9 are thought to share the MyD88-dependent pathway that activates interleukin-1 receptor-associated kinases (IRAKs) and TRAF6 located downstream (Kawai & Akira (2005) Arthritis Res. Ther. 7, 12-19). These, in turn, activate NF-KB and mitogen-activated protein (MAP) kinases, leading to activation of inflammatory cytokine genes. Thus, TLR agonists activating TLR7/9 or other TLRs may act to protect against lethal infection with glanders.

In summary, in the diseases described above, the pathogenesis of HIV, *Yersinia*, *Burkholderia*, filoviruses, and tularemia all involve antigen-presenting cells being infected with a pathogen, which they then transport to regional lymph nodes where pathogen replication occurs. As an example, the in vitro infectious disease model can be comprised of two modules: an infection module, where the macrophages/DCs are infected by the pathogen, which can be represented in model systems of the present invention by the VS, and the disease module, which represents the process whereby infected APCs transport the pathogen to regional lymph nodes, which can be represented in the model systems of the present invention by the LTE. In this disease model module LTE, the lymphocytes are activated/primed and the pathogen multiplies, as occurs naturally in a human lymph node. For this category of pathogen, the LTE itself may serve as the disease model module rather than needing a separate engineered tissue construct as with, e.g., a tumor disease model. Optionally, one could use the AIS to generate an immune response to a potential vaccine candidate and then transfer the contents of the non-infected, primed LTE to an infected LTE disease model module to determine the effect of the vaccine candidate on viral replication and infection, and the effect on immune clearance of the infection. Because the present invention is modular, with both infected and uninfected VS and LTE modules, and the modules can be used in different combinations and sequences, a practioner may select different embodiments to investigate different effects on viral replication, infection, and pathogenesis resulting from different antigens, adjuvants, vaccines, drugs, and other agents, depending on whether the effect sought is prophylactic, therapeutic, or both, and depending on the desired site of immunity (e.g., peripheral tissue, lymphoid tissue, or both). Indeed, some embodiments of the invention may use only a modified VS or LTE as the entire disease model for certain types of disease.

EXAMPLES

The artificial immune system of the present invention can be used to study many human diseases, including HIV. This in vitro model can not only be used to model bacterial and viral disease systems, but also used to study host immune responses in injury and inflammation.

Example 1

Figure 1:
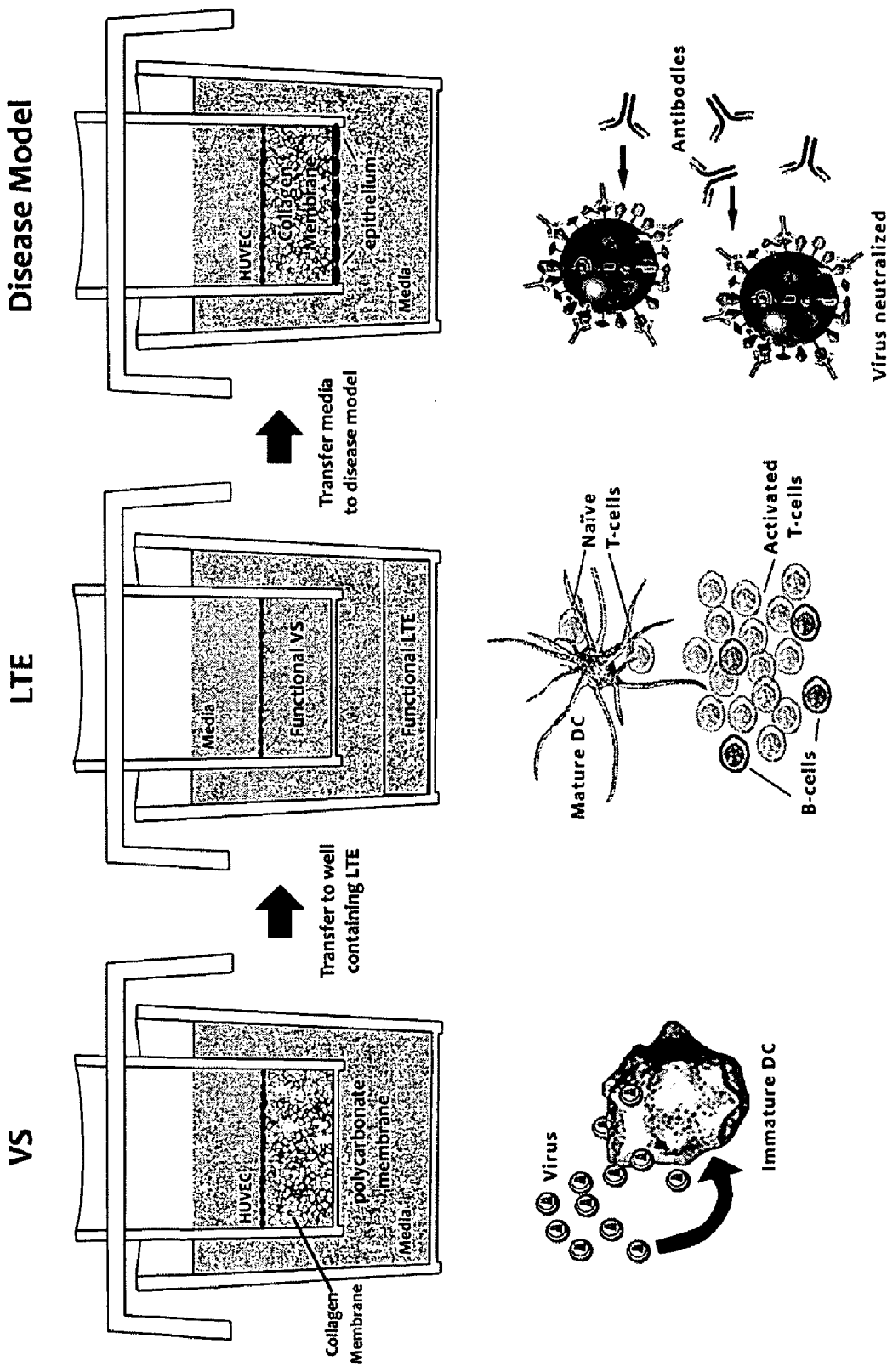
FIG. 1. Schematic illustration of an embodiment of the invention, showing the integration of the AIS and a disease model.
Figure 2:
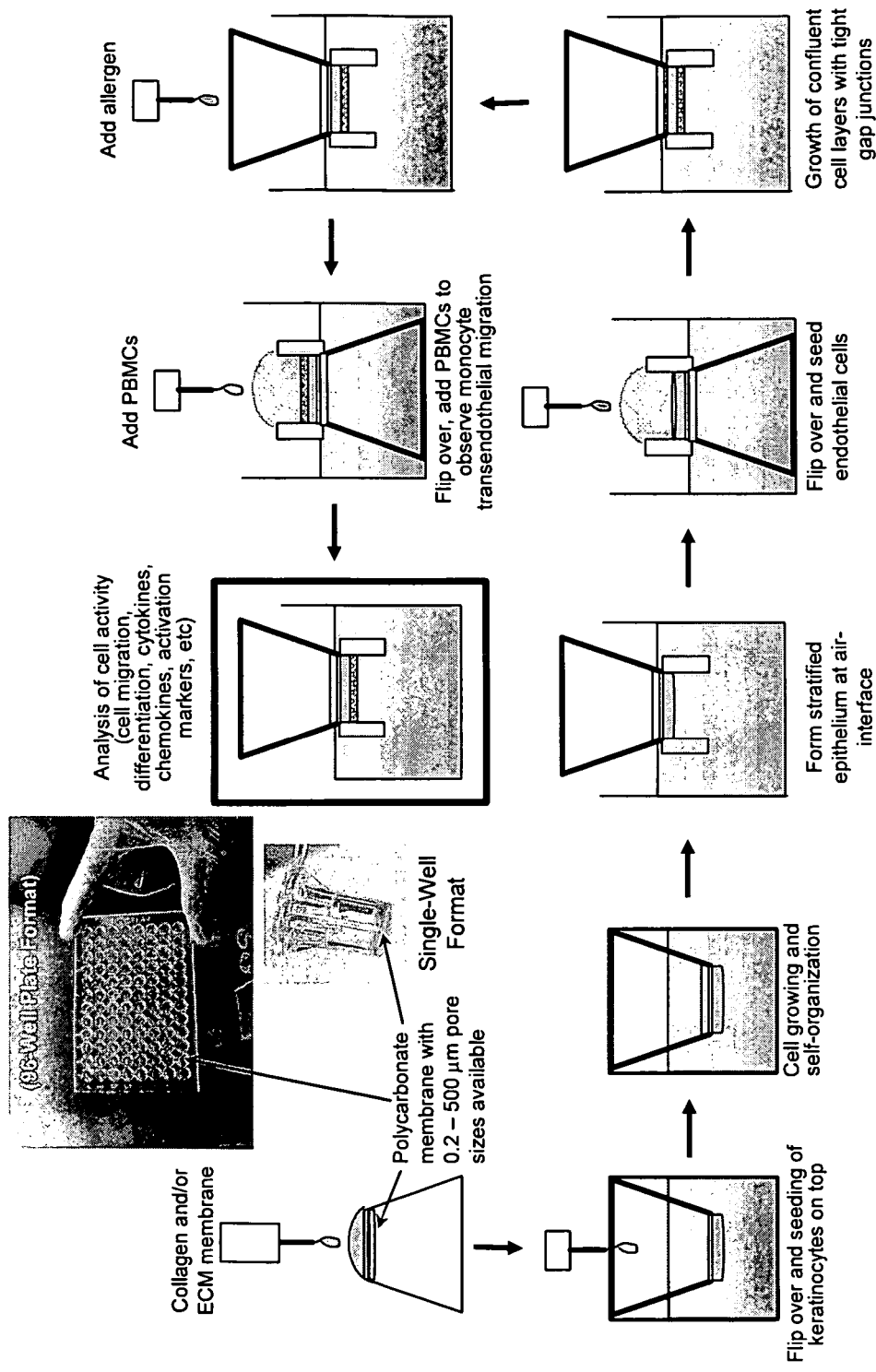
FIG. 2. A 3D heterogeneous tissue construct, comprising the addition of cells on the top and bottom of the construct, to create endothelial and epithelial layers.

Generic tissue construct for a 3D in vitro disease model. FIG. 2 illustrates a 3D heterogeneous tissue construct, comprising the addition of cells on the top and bottom of the construct, to create endothelial and epithelial layers. This model is an improvement on our established 3D endothelial cell-only construct, which has been used for transendothelial migration and for monocyte to dendritic cell and macrophage differentiation (the vaccination site, VS).

The 3D model of this example can be used to study immunophysiological reactions when subjected to various diseases and vaccine formulations. This is a generic construct because most tissues involve a 3D extracellular matrix with associated endothelial and epithelial layers. The disease, whether viral, bacterial, or tumoral, is introduced into the generic tissue construct. The various immunocytes and biomolecules from the AIS (e.g., antibodies, T cells, cytokines, chemokines) can then be delivered to the disease model to examine and detect effector responses (e.g., the presence or absence of neutralizing antibodies, cytotoxicity).

Example 2

Tumor modeling in the AIS using melanoma cells. Many in vitro model systems have been used for examining the effects of anti-cancer therapeutics and tumor growth in adult and childhood cancers, using both primary cells and various cell lines (see, e.g., Houghton et al. (2002) *Clin Cancer Res* 8, 3646-57). Such models have proven useful for assessing tumor metabolic states, inhibition of proliferation, and decreases in overall biomass (see, e.g., Monks et al., (1991) *J Natl Cancer Inst* 83, 757-66; Scherf et al., (2000) *Nat Genet* 24, 236-44).

Animal models of human cancers have not been good predictors of human therapeutic outcome because of species differences (see, e.g., Houghton et al., (2002) *Clin Cancer Res* 8, 3646-57; Bridgeman et al., (2002) *Cancer Res* 60, 6573-6; Batova et al., (1999), *Cancer Res* 59, 1492-7).

As with any tumor model, the primary end goal is to increase patient survival and overall well being and to decrease tumor burden. The most predictive model will aid in correlating between what is observed in vitro with what is observed in the clinical setting.

Melanocytes in human skin are inter-follicular melanin-containing (pigmented) cells within the epithelial stratum and are of neuroectodermal origin. Melanoma is a common form of human skin cancer. Malignant melanoma (both pigmented and non-pigmented forms) are frequently resistant to interventional therapies and are associated with significant morbidity and mortality.

Two modes of melanoma cellular proliferation are known to occur: one in a radial direction and the other in a vertical direction, into the subepithelial matrix (dermal layer in vivo) (Chudnovsky et al., (2005) *Nat Genet* 37, 745-9). Many factors have been implicated in spontaneous, uncontrolled proliferation including genetic alterations, overexpression of the catalytic subunit of human telomerase reverse transcriptase (TERT) and expression of melanoma markers HMB-45 and Melan-A. Pagetoid invasion into upper epithelial and dermis layers is typically observed under these conditions. Various melanoma cells can be purchased from ATCC (e.g., A-375, SK-MeI-31, WM115, SK-MeI-2, SK-MeI-24) with varying characteristics as to invasion properties (vertical or radial) and expression of specific human melanoma markers (e.g., NRAS, PI3K, CDK4, HMB-45 or Melan-A).

Example 3

Figure 3:
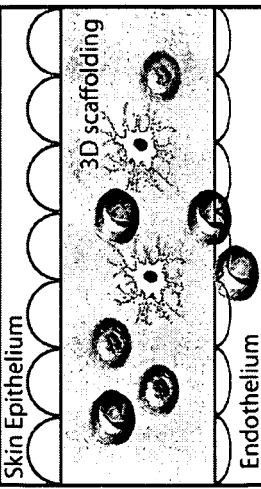
FIG. 3. A schematic representation of the development of a generic disease model and how it can be tested with a particular disease.

Heterogeneous tissue constructs with the addition of cells on the top and bottom of the tissue construct to form endothelial and epithelial layers. A schematic representation of the development of the generic disease model and how it can be tested with a particular disease is shown in FIG. 3. As an example, we used a polycarbonate membrane support structure to prepare a 3D ECM matrix, comprising either collagen, synthetic or natural materials (e.g., hydrogels, PLA, PLGA, gelatin, hyaluronic acid), or combinations thereof. We have established an ECM that is capable of supporting two cell layers. We first grow a layer of epithelial cells (e.g., human keratinocytes) on one side of the matrix. An advantage of this model is that other epithelial cells can be used, such as respiratory epithelial cells, skin epithelial cells, or intestinal/oral epithelial cells (as schematically illustrated in FIG. 3). The basement membrane zone between the epithelium and the matrix is important to the success of this aspect of the construct and additions, such as collagen types IV or VII can be included. For a melanoma model the barrier function of the basement membrane may also be important in dissecting the pathology of modes of metastasis. This is an advantage of the general architecture of the disease model of the present invention; it can be used to mimic many tissues by using different epithelial cell types. After melanocyte and keratinocyte seeding and when the keratinocytes have become established and begun stratification, the cells are exposed to an air interface, to encourage continued stratification, formation of tight cell junctions, and keratinization.

When a keratinized cell layer is formed, the construct can be inverted, so that a layer of endothelial cells (e.g., HUVECs, immortalized endothelial cell lines) can be applied to the other side. When the endothelial cells have established, the construct can be inverted (so it will be upright again) to reinstate the air interface for the keratinocytes. When the endothelial cells form a confluent monolayer, the tissue construct is complete and ready for characterization.

In other embodiments of the present invention, in a multi-functional disease model without melanocytes in epithelial layer, a viral or bacterial disease model can be prepared. In these embodiments, either the viral or bacterial component is applied to the specialized, non-keratinized epithelial surface, mimicking normal physiologic events. In viral and bacterial invasion/infection, epithelial compromise is caused by either cellular infection or release of bacterial toxins, which can also be monitored.

Example 4

Viability of the 3D generic disease tissue constructs. Studies of keratinocytes have shown the cells to remain viable in culture for several weeks (Boelsma et al., (2000) *Acta Derm Venereol* 80, 82-8). We also have experience of maintaining HUVECs in culture and on a 3D construct for several weeks.

Viability of the cells on the construct can be monitored by, for example, such methods as identifying any morphological changes and by the classic LDH release assay. As cells die, the plasma membrane becomes leaky with LDH being released into the culture medium and can be measured with a coupled enzymatic assay that results in the conversion of resazurin into a fluorescent resorufin product. The amount of fluorescence produced is proportional to the number of lysed cells. Cell staining can also be performed on the tissue constructs to measure live/dead cell populations. Cell-permeant esterase substrates, such as CellTracker Green CMFDA, serve as viability probes that measure both cell membrane integrity, required for intracellular retention of the probe, and enzymatic activity, required to activate the fluorescence of the probe. Cell-impermeant nucleic acid stains, such as ethidium homodimer-1, can be used to detect dead cells. Fluorescently stained cells can then be observed by confocal microscopy.

Example 5

Epithelial cells form stratified layers on the constructs. For the construction of the skin equivalent model, the keratinocyte layer is exposed to an air interface to encourage formation of stratified layers. The formation of the stratified layers can be monitored by microscopic examination. Periodically cell layers can be examined by using immunofluorescence confocal microscopy to identify the tight junctions and nuclei of the cells. Additionally, samples can be fixed in paraformaldehyde, embedded in paraffin, cut into sections, and stained with haematoxylin and eosin for light microscopic examination.

Example 6

Construction of a generic tissue module creating an in vitro disease model. In embodiments of the present invention, the 3D model is examined to observe immune- or inflammation-mediated responses to various diseases (e.g., tumors models). As examples, melanoma cells, HSV, influenza virus, *Escherichia coli*, and *Staphylococcus aureus* are used.

Melanoma cells are incorporated when the epithelial layer is formed. As human melanocytes are interfollicular, basal epithelial cells, using a cell line that is slower growing allows keratinized epithelial formation. Application of different cell types can be accomplished by intermixing these cells with normal keratinocytes (for example, at a ratio of ~$5\times10^3$ to ~$30\times10^3$). Monitoring of the vertical and lateral spread of the malignant melanocytes can be accomplished by staining with fluorochrome-labeled, melanocyte-specific markers and confocal microscopy. As another example, other constructs can be digested and the number of melanocytes present can be assessed using flow cytometry and similar markers.

Example 7

Figure 4:
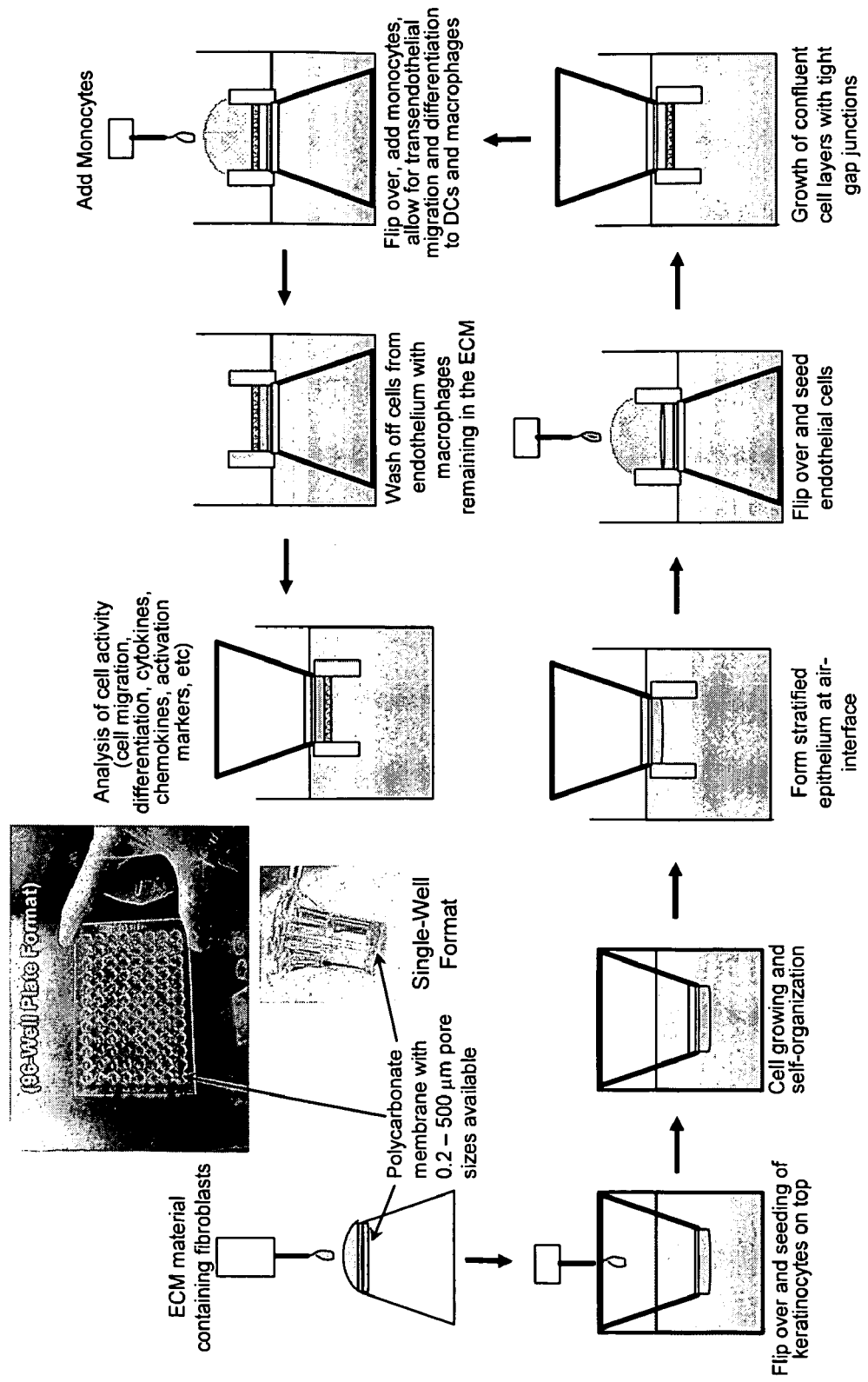
FIG. 4. Schematic illustration of, as an example, vertically expanding melanoma tumor cells or bacterially or virally infected fibroblast cells inside the 3D construct.

As an example, a methodology that can be used to add vertically expanding melanoma tumor cells or bacterially or virally infected fibroblast cells inside the 3D construct, is illustrated schematically in FIG. 4. To add tumor cells to the disease model, we mix these cells within the ECM material before it is added to the membrane support and before we begin to grow the epithelial and endothelial cells on the matrix.

Example 8

For the preparation of a viral model, there are several relevant methods. As an example, for a live virus, we would infect an epithelial layer. As another example, virus-infected irradiated fibroblasts can be incorporated in the collagen matrix. HLA-matched, syngeneic or autologous fibroblasts can be used; they can be propagated and infected with virus at an appropriate multiplicity of infection (MOI) (e.g., ~10). Infection is allowed to proceed until an appropriate time post-infection, at which time infectious virus is UV-inactivated.

Example 9

In vitro infection/disease models are important for an analysis of the viral life cycle, including attachment, entry, and uncoating, and to unravel the interactions between viral particles and host target cells. We can also use the in vitro disease/infection model to examine the efficacy of the vaccine-induced immune products created in the AIS. Suitable example viral disease models include Herpes simplex viruses (HSV) and influenza viruses. Human and/or murine model systems can be used.

Example 10

The present invention comprises both two- and three-dimensional (2D, 3D) models of infection/immune induction. In an example 2D model, a static culture system can be employed. In an example 3D model, the vaccination site (VS) and lymphoid tissue equivalent (LTE) can be used.

Example 11

Several methods of viral antigen introduction are suitable for practicing the present invention. As an example, direct infection of cultured epithelium with virus at an appropriate multiplicity of infection (MOI) can be used. As another, example, HLA-matched or syngeneic fibroblasts can be used; they can be propagated and infected with virus at an appropriate MOI (e.g., ~10). Infection will be allowed to proceed until an appropriate time post-infection at which time infectious virus will be UV-inactivated. The kinetics of virus infection and inactivation can be confirmed by, for example, immunofluorescence and plaque assay, respectively.

Infectious virus or virus-infected UV-inactivated fibroblasts can be added to the cultures. For fibroblast cultures, uninfected UV-treated fibroblasts can be used as negative controls. In 2D cultures, infectious virus, fibroblasts or vaccine/adjuvant formulations are added to a mixed immunocyte population containing antigen presenting cells (APCs) and lymphocytes. For 3D culture, antigens are introduced into a vaccination site (VS) containing reverse-transmigrated (RT) antigen presenting cells (APCs), comprising dendritic cells (DCs). APCs then process the antigen and are introduced into the lymphoid tissue equivalent (LTE), comprising T and B lymphocytes.

In both 2D and 3D cultures, immunological parameters of interest include patterns of immunocyte phenotype and cytokine synthesis and secretion. Flow cytometric analysis is valuable in this regard. Virus-specific cytotoxic activity can be assessed for T cells using, for example, a non-radioactive LDH cytoxicity assay with virus-pulsed target cells. B cells can be evaluated for specificity and isotype of antibody secretion, as well as neutralizing capability.

To evaluate recall responses and anti-viral activity, immunocytes and/or soluble factors can be recovered from 2D cultures or from the LTE of the 3D system for analysis. These immunocytes and/or biomolecules can then be tested, for example, using an in vitro 2D, an in vitro 3D tissue engineered disease model, or an in vivo (especially murine) disease model. In 2D experiment, these can be co-cultured with, for example, suspension or monolayer cultures of fibroblasts. The cultures can then be challenged with infectious virus or virus-infected UV-inactivated cells. As another example, a similar in vitro challenge can be performed in the 3D tissue engineered disease model incorporating an epithelial layer. In the in vitro experiments, cultures are harvested at selected times post-challenge and assayed for virus-specific immunity and anti-viral activities, as indicated, for example, by titers of infectious virus recovered.

To assess the in vivo efficacy of immunocytes derived from the LTE, we can conduct adoptive transfer studies in, for example, a mouse model where selected cell populations derived from the AIS can be introduced prior to viral challenge. Several murine models of HSV infection are available and can be used to assess protective efficacy of cells recovered from the AIS.

Example 12

As another example of the present invention, we can conduct an 'experiment of nature' involving seropositive individuals with recurrent HSV ($S^+R^+$), seropositive individuals without recurrent disease ($S^+R^-$) and seronegative ($S^-R^-$) human subjects. Cells from these subjects can be sensitized with viral antigens. Subsequent immunological read-outs can allow for discrimination of primary and recall immune events and immune profiling of protective immune mechanisms when comparing $S^+R^+$ and $S^+R^-$ subjects.

Example 13

In a melanoma tumor model, the spread of the melanocytes radially through the epithelial layer and penetration into the sub-epithelial matrix (vertical tumor expansion) can be examined. As some melanoma cell lines exhibit radial expansion only (possibly the result of the impediment of the basement membrane structure or biochemical makeup of the different collagens) or vertical expansion only, it is possible to target the immunocyte population within the matrix. The presence of melanoma antigen with or without the addition of adjuvants, will lead to the maturation of DCs that have captured antigen.

As the APCs reverse transmigrate out of the module with captured antigens, they can be matured with TNFα. APC phenotypic markers and a panel of inflammatory cytokines can be compared to modules without melanoma cell additions. These results can then be compared to VS responses with known stimulants or adjuvants (such as LPS, CpG, poly (IC), MF59). Functional assessment of these monocyte-derived APCs after exposure to tumor antigens from the melanoma cells in the VS, can be conducted by placement into the LTE module for assessment of antigen presentation. IL12 is an important cytokine released by DCs activating T helper cells, which then release IFNγ. IFNγ contributes to CTL activity and B cell differentiation into plasma cells. Antibody release, compliment fixation, and influx of PMNs to the region of the tumor cells (in vivo) causes release of TNFα. TNFα and IFNγ have tumor cytostatic properties. (Croci et al. (2004) *Cancer Res* 64, 8428-34) and can be monitored. As an example, a non-radioactive cytotoxicity T cell assay monitoring LDH release can be used.

Example 14

Figure 5:
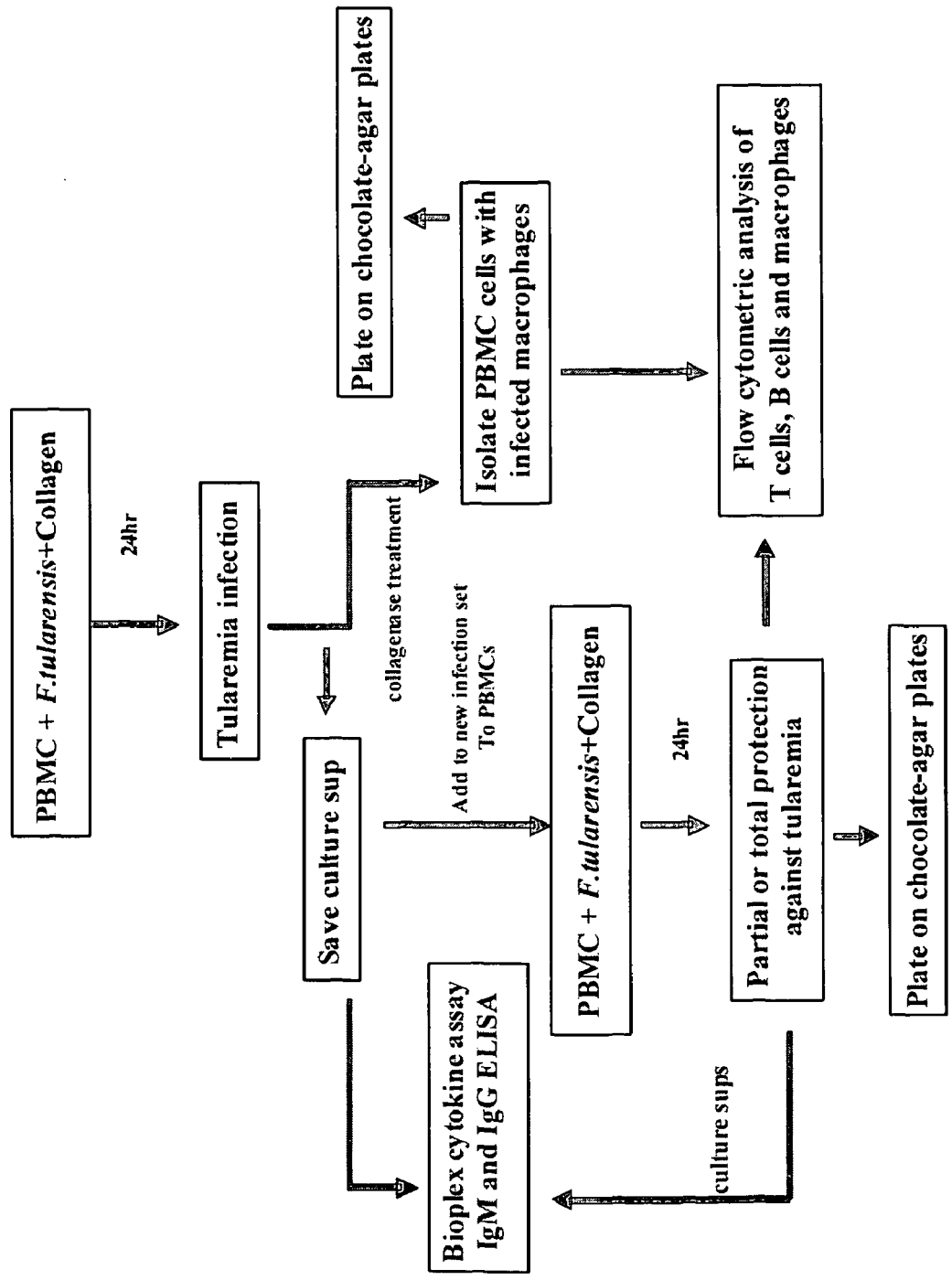
FIG. 5. Flow chart for preparation and analysis of an in vitro tularemia model.
Figure 6:
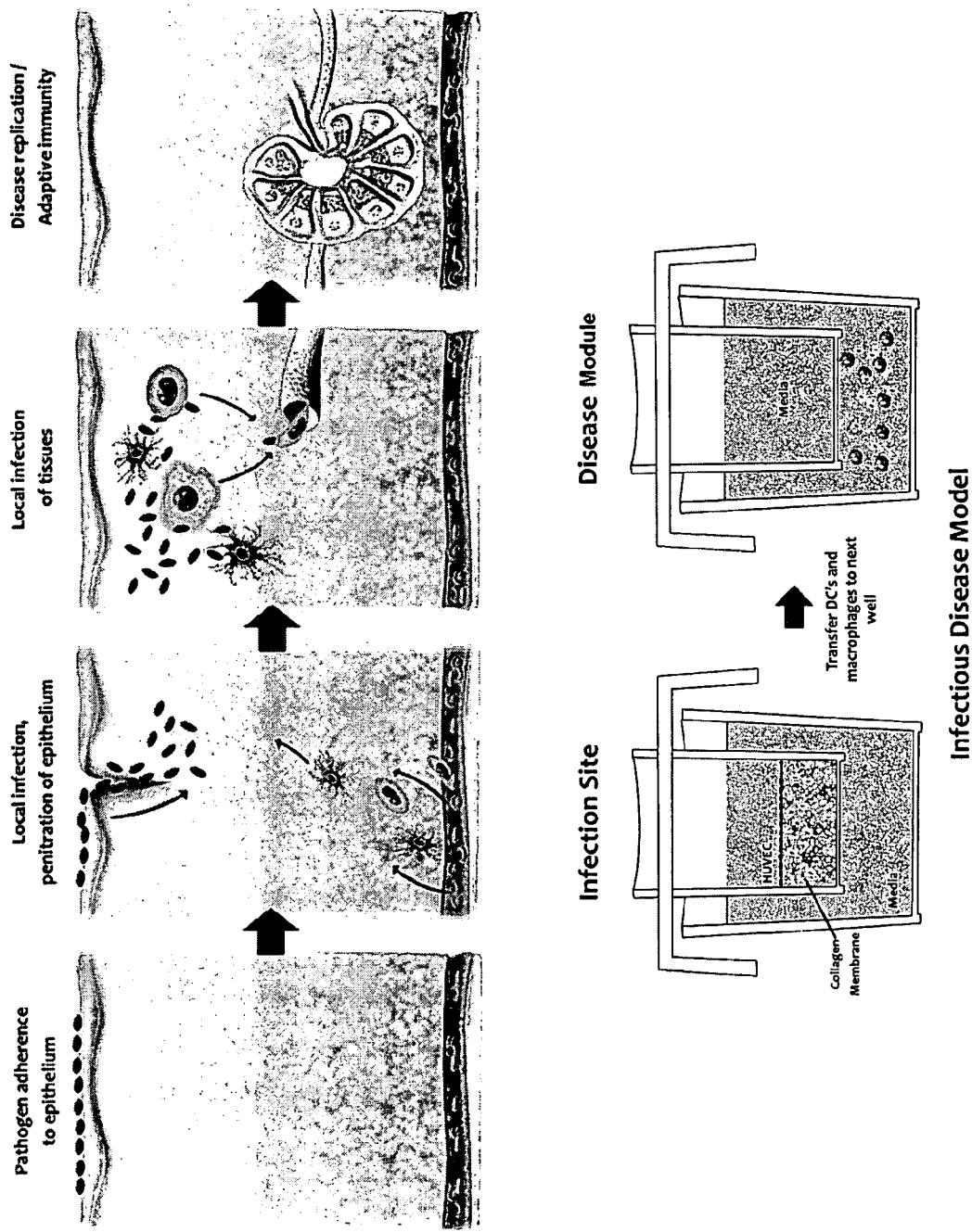
FIG. 6. An example in vitro disease model architecture.
Figure 7:
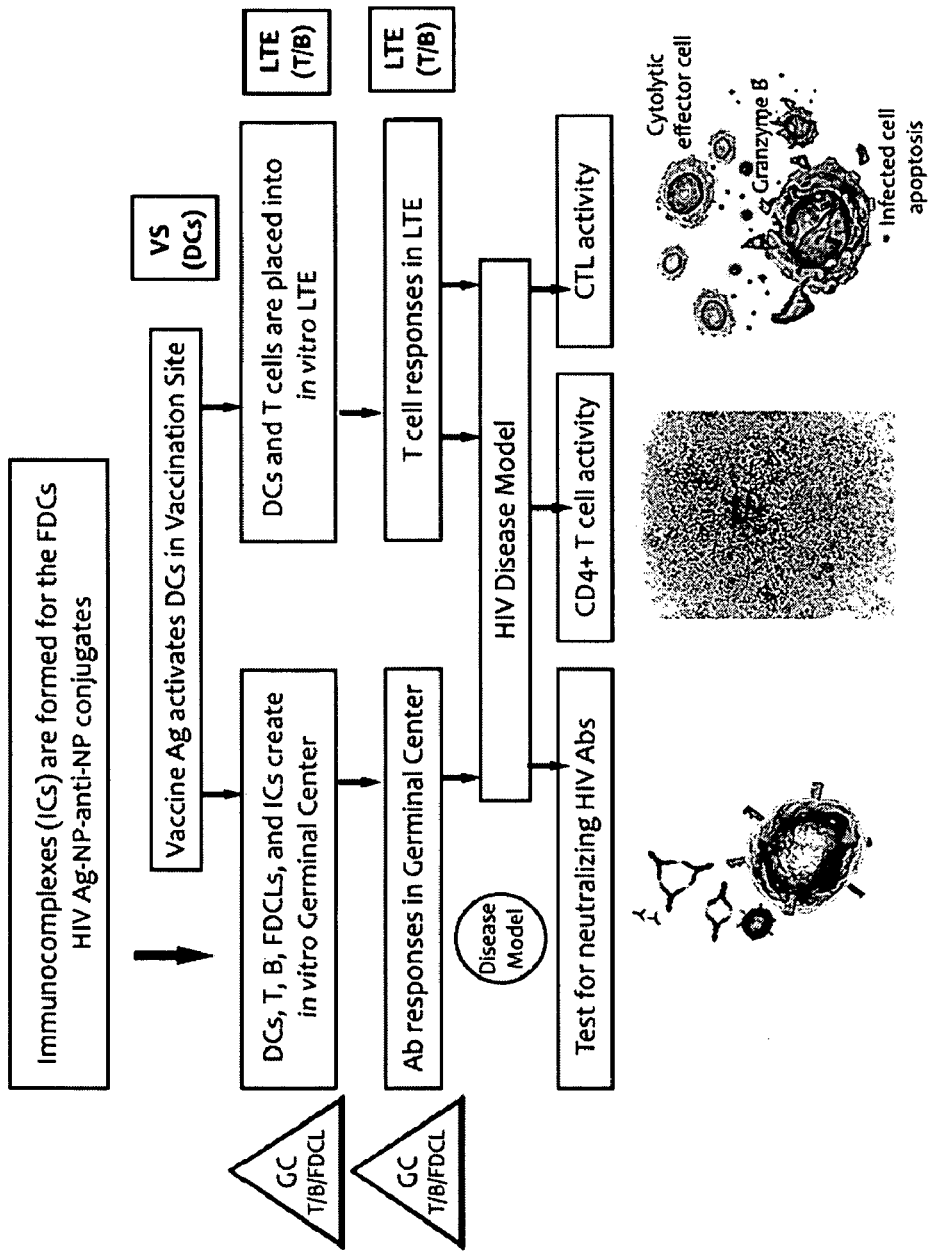
FIG. 7. HIV vaccine candidate testing flow chart.
Figure 8:
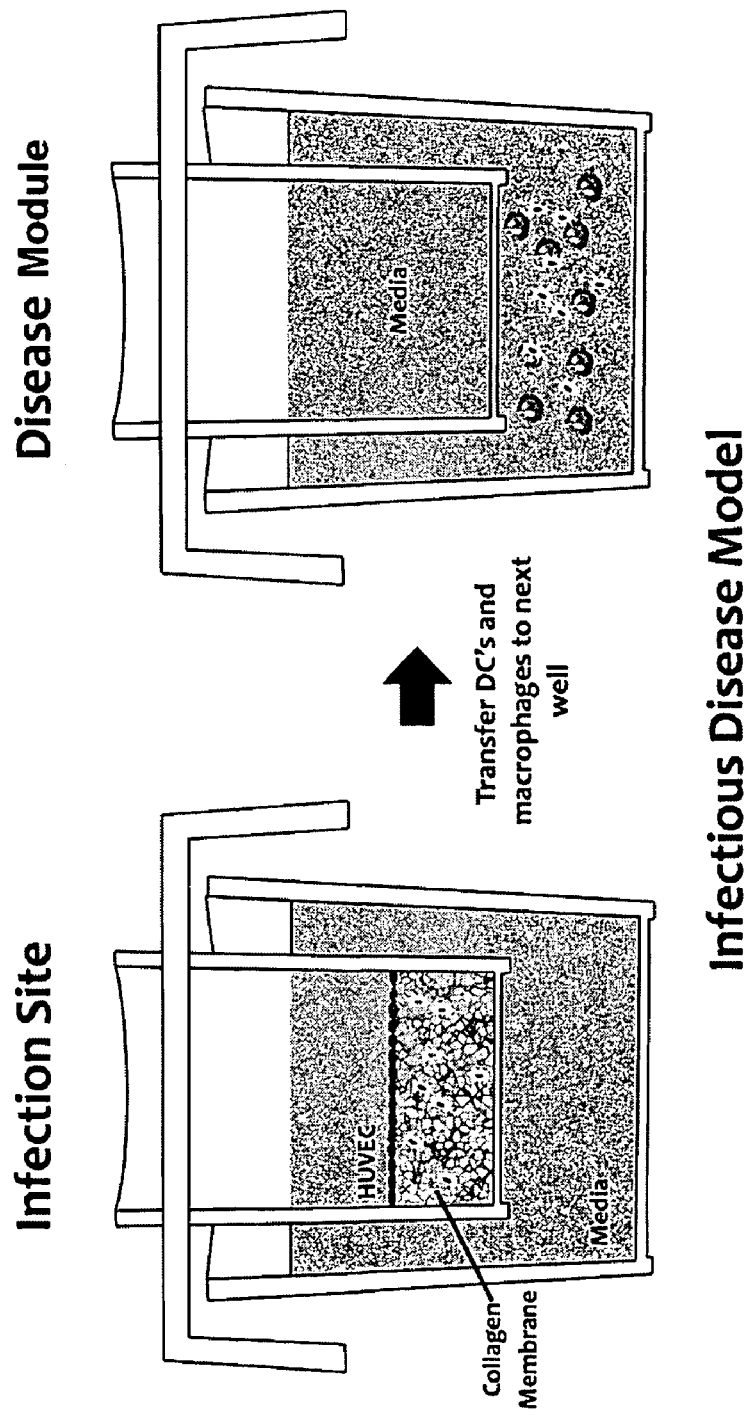
FIG. 8. HIV disease model for testing HIV vaccine candidates. A candidate vaccine is placed in the VS module to prime APCs. These APCs are then placed in the LTE module to prime lymphocytes. The in vitro-immunized lymphocytes and resulting antibodies are placed in the disease module along with infected APCs (obtained from a parallel infection with HIV in the infection site module). Autologous cells are used. Any protection offered is quantitated, for example, by inhibition of viral replication or cell lysis.
Figure 9:
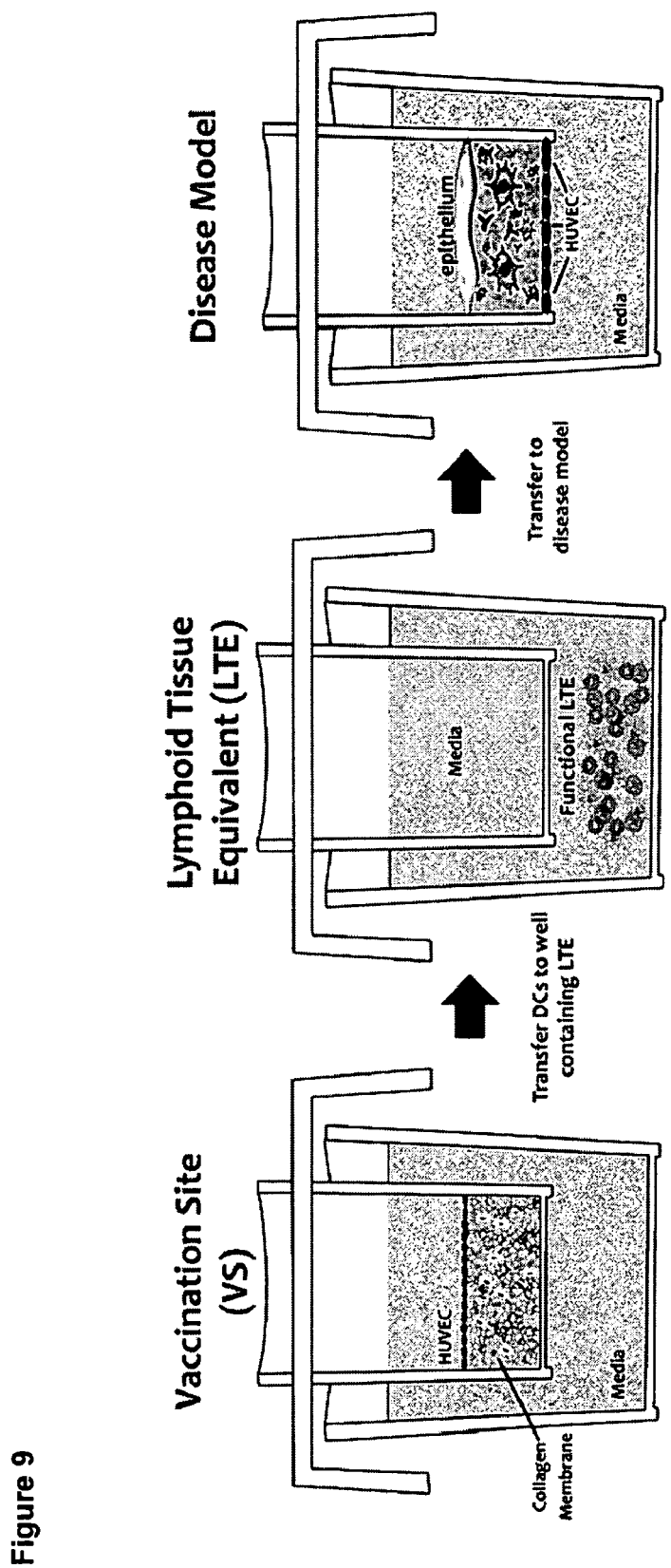
FIG. 9. Assessment of correlates of protection in an infectious disease. All elements of correlates of protection (CTL, antibodies, cytokines, $CD4^+$ T cells) are examined.
Figure 10:
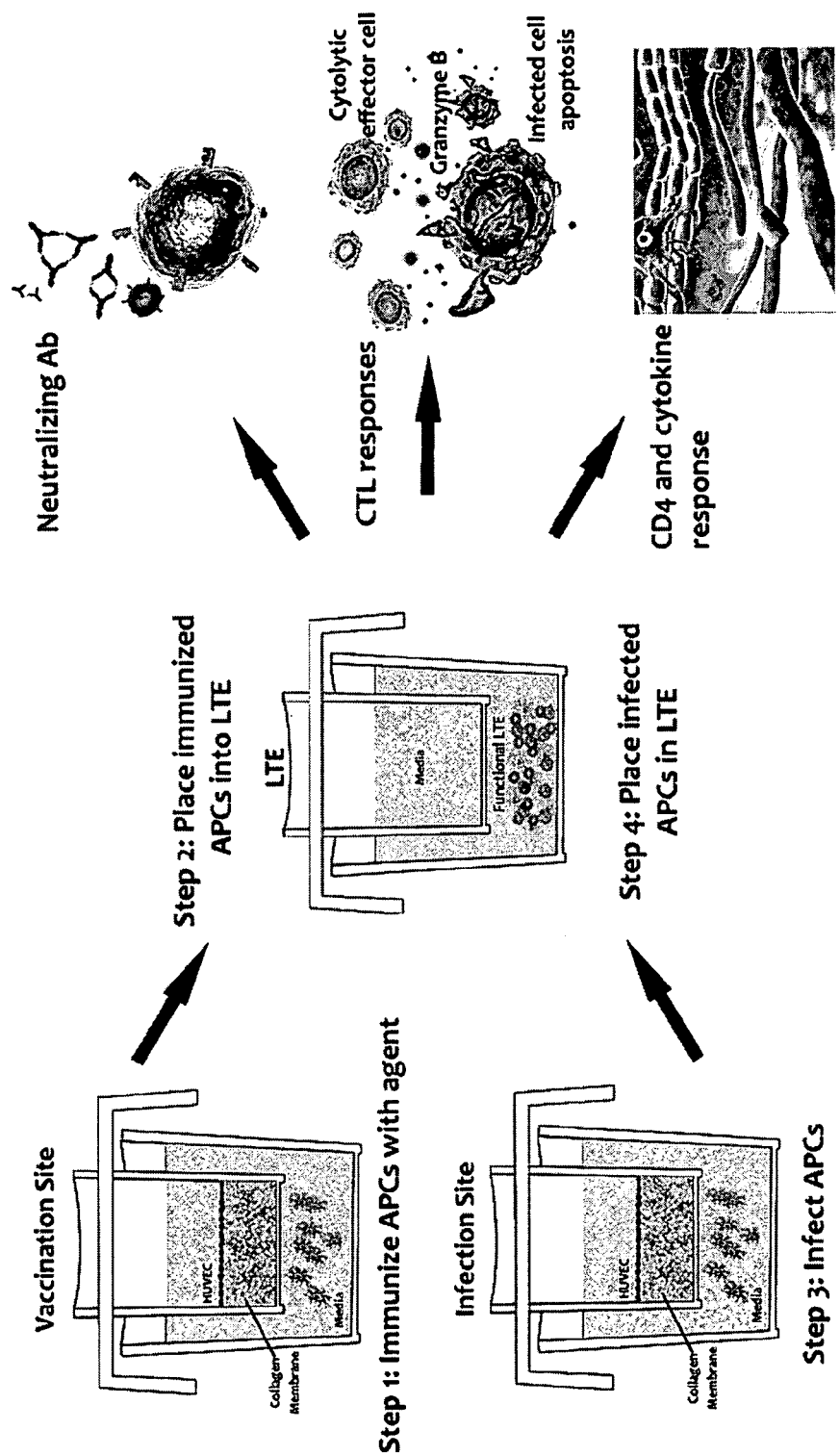
FIG. 10. Diseased cells (e.g., HIV-infected APCs) would be exposed to 'output' from the VS/LTE combination by putting the diseased cells (e.g., HIV-infected APCs) from the VS into the LTE to evaluate the effect on the diseased cells. The effects on the LTE components by the diseased cells can be assessed, as can any effect on the diseased cells to define the correlates of protection.

Tularemia model. In an embodiment of the invention, an in vitro model of tularemia is prepared. Live attenuated strains can be safely used in a BSL-2 laboratory. PBMCs from a series of human blood donors are prepared and mixed with different ratios of *F. tularensis* in a collagenous 3D matrix. The immune response to *F. tularensis* is then assessed, using, for example, the Bioplex 22-cytokine kit. For example, levels of IL-18, IL-1β, IFN-γ, IL-12, IL-4, and IL-5 are determined. IgM and IgG antibody ELISAs are conducted on culture supernatants to examine the humoral response. The collagenous construct is digested with collagenase to release the cells, and aliquots are serially diluted and plated on chocolate-agar plates. Colonies are counted after ~3 days to determine the multiplication of pathogen in host cells. The activation state of T cells, B cells, and macrophages in response to infection is determined by, for example, FACS analysis. A flowsheet of the experiment is shown in FIG. 5.

To determine whether protection is offered by secreted antibodies, the culture supernatants from first infection are added to a new set of PBMCs and *F. tularensis* in collagen to permit a new infection. This is followed by determining cytokine levels, ELISA, flow cytometric analysis, and colony counts, as described above. Any protection offered by antibodies is expected to be reflected in increased protective immune responses and lowering of pathogen colony counts.

This in vitro model can be used as test bed for vaccine and drug candidates. Quinolone drugs, such as ciprofloxacin, have been reported to be effective against tularemia (Johansson et al. (2002) Scand. J. Infect. Dis. 34, 327-30). The effect of such drugs can readily be tested by the addition of the drug to the in vitro model and determining any reduction in colony counts. Similarly, other drugs and vaccine candidates could be assessed for efficacy in this model system.

Example 15

Filovirus models. The vaccination site (VS) module of the artificial immune system of the present invention, comprising a confluent endothelium with monocytes and macrophages, can be used as a pathogenesis model system. For the disease module, the VS and Infection Site (IS) modules can be used interchangeably, unless otherwise noted. To prepare a filovirus disease model, as an example intracellular viral pathogen, IS modules are prepared and serve as infection targets. Preparation of the IS module comprises growing a monolayer of endothelial cells over a collagen matrix. PBMCs are added on top of the endothelial cell layer. Monocytes preferentially extravasate across the endothelium into the collagen matrix, with some T and B cells (5-10%). Monocytes in PBMCs differentiate into APCs of a range of phenotypes as they traverse the endothelium. Some monocytes differentiate into mature and immature dendritic cells (DCs) and then reverse transmigrate across the endothelium from the collagen, while other monocytes differentiate into macrophages and these sub-endothelial cells remain in the collagen matrix. The system models the in vivo differentiation process, whereby APCs (e.g., monocytes) entering a site of vaccination obtain differentiation signals as they cross the endothelium into the tissue. This method is superior to the widely used cytokine-induced (e.g., GM-CSF, IL-4, MCSF) methods of generating DCs and macrophages from PBMCs.

Infectious virions can be added on top of the endothelial cells. Filoviruses will infect the endothelium and also migrate across it to infect DCs and macrophages in the collagen. Additional lymphocytes can then be included in the collagen to mount an immune response against the pathogen.

Thus, the VS module/infection site (IS) module is the essential element of the Ebola disease model, the only difference is that we will incorporate additional lymphocytes. The system can be incubated for different time periods to study progression of disease. Although endothelial cells are an important part of the IS system, the presence of endothelial cells in the system may generate MHC-I-mediated allogeneic responses in response to Ebola virus or VSV expressing Ebola viral proteins or the vaccine candidates. If they do, APCs are isolated from the IS module after 48 h (when DCs and macrophages have differentiated in the IS) and add them with fresh PBMCs in the LTE module/disease module for stimulation. If the endothelial cells do not generate allogeneic responses, we will continue to use the IS as the disease module.

Thus, the VS/IS module of the artificial immune system of the present invention closely mimics the in vivo scenario of infection; all of the components involved in the infection process, including endothelial cells, DCs, macrophages and lymphocytes, are present in the model system. The system can be incubated for different time periods to study progression of disease. Cytokine profiles are assessed using, for example, a Bioplex assay and antibody responses are assessed by, for example, ELISA at different time points using culture supernatants from this model. For example, levels of IFNα, IL-6, MCP-1, MIP-1a, MIP-1b, IFN-β, IFN-γ, IL-18, and TNF-α are determined. Disease-associated factors, such as TF, can also be measured. The collagen matrix is digested with collagenase to release the cells; their apoptotic state and expression levels of different cellular markers on endothelial cells, DCs, macrophages, and lymphocytes are assessed by, for example, flow cytometry. Antibodies generated can also be assessed.

To assess the efficacy of filovirus vaccines, PBMC cells from a series of human blood donors are incubated with different concentrations (e.g., ~1-50 µg/mL) of, for example, Ebola vaccine in the VS module and in a simple collagenous 3D matrix and are incubated for different time periods. The vaccine formulation will be taken up by monocytes, in a similar way to infectious virions, resulting in the establishment of a host immune response to the vaccine antigens. This host immune response to the test vaccine is then assessed in terms of, for example, cytokine responses, using, for example, the Bioplex 22-cytokine kit. For example, levels of IFNα, IL-6, MCP-1, MIP-1a, MIP-1b, IFNβ, IFNγ, IL-18, and TNFα are determined. IgM and IgG antibody ELISAs are conducted with culture supernatants to determine the levels of antibody production in response to the test vaccine. The collagenous construct is digested with collagenase to release the cells and the activation and apoptotic state of T cells, B cells and monocytes, macrophages, and dendritic cells in response to infection are determined by FACS analysis. Experiments using vectors expressing different viral proteins, peptides, and combinations of proteins can also be used to assess differences and variations in the host immune responses to viral proteins.

Example 16

Yersinia model. An embodiment of the present invention comprises a disease model of Yersinia pestis infection. In an infection module (e.g., the IS), macrophages are infected by the pathogen. The disease module models the process by which infected macrophages transport the pathogen to the regional lymph nodes. In this disease module, the lymphocytes are activated/primed and the pathogen multiplies. This lymph node equivalent (LTE) module serves as the disease module. In vivo, the bacteria replicate in lymph nodes before migrating to other organs. The artificial immune system of the present invention is flexible in that the various modules are designed as plug-and-play immunological constructs. This feature is exploited here with infection and disease modules of the Yersinia infectious disease model.

The infection module system (IS) involves growing a monolayer of endothelial cells over a collagen matrix. PBMCs are added on top of the endothelial cell layer. Monocytes preferentially extravasate across the endothelium into the collagen matrix with a small number of T and B cell lymphocytes (5-10%). The monocytes in the PBMCs differentiate into APCs of a range of phenotypes as they traverse the endothelium. Some monocytes differentiate into mature and immature dendritic cells (DCs) and reverse transmigrate across the endothelium from the collagen, while other monocytes differentiate into macrophages and these sub-endothelial cells remain in the collagen matrix. This system mimics the in vivo differentiation process, where antigen-presenting cells (e.g., monocytes) entering the site of vaccination receive differentiation signals as they cross the endothelium into the tissue.

To prepare the disease model, Y. pestis is added at different multiplicities of infection (MOI) on top of the endothelial cells of the IS module. Y. pestis crosses the endothelium and enters the collagen where the pathogen will infect the macrophages and also pulse the dendritic cells with Y pestis antigens. After 4-6 h of infection, the collagenous matrix is digested to release the APCs.

These infected APCs from the IS are then transferred to the disease module (LTE) where they are added with autologous PBMCs and can be co-cast in collagen. The lymphocytes in collagen mount an immune response against the pathogen. The system can be incubated for different time periods to study disease progression. The disease manifestation is observed in terms of, for example, the development of severe necrotic inflammation, macrophages and dendritic cells undergoing apoptosis as a result of infection and inflammation, and the host immune system mounting an immune response to contain the infection. Containment of infection will be reflected as reduction in bacterial counts. Host macrophages, DCs, and lymphocytes will secrete pro-inflammatory cytokines and chemokines and antibodies in response to the infection.

Parameters of disease pathogenesis will be determined as follows. Collagen constructs from the disease module are paraffin-embedded followed by sectioning and microscopy to examine the inflammatory lesions. Collagen is digested with collagenase to release cells, which are then assayed for apoptotic and other cellular expression markers by flow cytometry. This will provide information about host cell death and the activation profile of the immune cells due to the infection. An aliquot of the collagenase digest will be plated on nutrient agar plates to determine the colony forming units (cfu) and hence survival and multiplication of pathogen in the host cells and containment of the infection. Culture supernatants are assayed for cytokine and antibody secretion. The cytokine profiles are determined by, for example, a Bioplex assay and antibody responses are assessed, for example, by ELISA at different time points. For example, levels of IL-6, MCP-1, IL-12p35, IFNγ and TNFα can be determined. IgM and IgG antibody ELISAs are conducted using culture supernatants to determine the levels of antibody production in response to the infection.

In further embodiment of the present invention, the infectious disease model is used to test potential therapeutic methods that may cure the infection, pre- and/or post-exposure. The model can also be used to address basic questions related to bacterial pathogenesis.

The effects of various TLR agonists and vaccine adjuvants have been examined using the VS system. It has been reported that human monocytes infected with *Y. pestis* express cell surface TLR9 and differentiate into dendritic cells (Shaikh 2004). The effects of CpG and/or other adjuvants and *Y. pestis* infection in modulating DC function as APCs and on ability to contain the infection, can readily be tested in the model system of the present invention by pretreating the infection module with TLR agonists for 24-48 h, followed by introduction of the pathogen for 4-6 h. Infected APCs are taken out of the infection module and are then added to the disease module for different periods. The collagenous matrix from the disease module is digested with collagenase. The protection offered by, for example, adjuvants can be quantitated by plating the collagenase digest (as described above) and estimating the reduction in cfu.

Cytokines play important roles in the control of infection. Extraneous IFNγ and/or TNFα or IL-12 can be added in different concentrations to the disease module together with APCs from the infection module. The control of infection can be studied, for example, in terms of reduction in cfu by, for example, plating method and by, for example, determining cytokine and antibody levels in culture supernatants.

The TTSS and Yops are important for *Y. pestis* pathogenesis, as discussed earlier. Their effects can be tested in the infection module by adding these antigens to it and transferring the affected APCs to the disease module and determining the ability to contain the infection, by, for example, measuring the reduction in cfu by, for example, a plating method.

Monoclonal antibodies have been produced against *Y. pestis* and have been reported to protect Balb/c mice against *Y. pestis* challenge (Eyles et al. (2007) Vaccine 25, 7301-6). The protective effect of these monoclonals can be tested in the disease module system by adding protective or therapeutic antibodies to it. The infected APCs from the infection module, together with protective antibodies and autologous PBMCs, can then be co-cast in the disease module for different periods. Protection by the antibodies is determined, for example, by reduction in cfu by, for example, a plating method. Additionally, antibodies in the culture supernatants in the disease module, produced in response to the infection, can be added to a new infection set and any protection offered can be determined, for example, by cfu reduction, using, for example, a plating method.

In another embodiment of the present invention, vaccine candidates, such as those using the F1 or V antigen, can be tested for efficacy by placing in vitro-immunized lymphocytes in the disease module. First, the vaccine is placed in the VS module to prime APCs. These APCs are then placed in the LTE module to prime lymphocytes, which will be used in the disease module. These in vitro-immunized lymphocytes are placed in the disease module along with infected APCs (obtained from a parallel infection with *Y. pestis* in another infection module). Autologous PBMCs will be used throughout. The protection offered can then be quantitated, by for example, reduction in bacterial cfu by, for example, a plating method.

Example 17

*Burkholderia* model. An embodiment of the present invention comprises an in vitro disease model of *Burkholderia mallei* using the artificial immune system, based on multidimensional interrogation of human leukocytes. The artificial immune system can rapidly provide information about the effects of an immunotherapy on human population subgroups (genetic diversity, HLA haplotypes, age, gender).

In the infection module (IS) of the artificial immune system of the present invention, macrophages are infected by the pathogen (the IS module). The disease module models the process whereby infected macrophages transport the pathogen to the regional lymph nodes. In this disease module, lymphocytes are activated/primed and the pathogen multiplies. This LTE module is the disease module of the in vitro system. The bacteria replicate in lymph nodes before migrating to other organs. The artificial immune system is flexible in that the various modules are 'plug-and-play; immunological constructs. This feature is exploited in an embodiment of the present invention, comprising the infection and disease modules of a *Burkholderia* infectious disease model.

Preparation of the Infection Site Module Involves Growing a Monolayer of Endothelial cells over a collagen matrix. PBMCs are added on top of the endothelial cell layer. Monocytes preferentially extravasate across the endothelium into the collagen matrix with a small number of T and B cells (~5-10%). The monocytes in the PBMCs differentiate into APCs of a range of phenotypes as they traverse the endothelium. Some monocytes differentiate into mature and immature dendritic cells (DCs) and reverse transmigrate across the endothelium from the collagen, while other monocytes differentiate into macrophages and these sub-endothelial cells remain in the collagen matrix. The system mimics the in vivo differentiation process whereby antigen-presenting cells (e.g., monocytes) entering the site of vaccination receive differentiation signals as they cross the endothelium into the tissue.

In the IS, cells are infected by adding *B. mallei* at different multiplicities of infection (MOI) on top of the endothelial cells. *B. mallei* crosses the endothelium and enters the collagen where the pathogen will infect the macrophages and also pulse the dendritic cells with *B. mallei* antigens. After 4-6 h of infection, the collagenous matrix will be digested to release the APCs.

These infected APCs from the IS will then be transferred to the disease module where they are added with autologous PBMCs and can be co-cast in collagen. The lymphocytes in collagen mount an immune response against the pathogen. The system can be incubated for different time periods to study disease progression. The disease manifestation is observed in terms of measurable events or parameters, such as development of necrotizing lesions, macrophage and lymphocyte death, by apoptosis, as a result of infection and inflammation, and the host immune response to contain the infection. Containment of infection will be reflected as a reduction in bacterial counts. Host macrophages, DCs, and lymphocytes will secrete proinflammatory cytokines and chemokines and also antibodies in response to the infection; these can also be assessed.

Parameters of disease pathogenesis will be determined. The collagen constructs from the disease module will be paraffin-embedded, followed by sectioning and microscopy to visualize necrotic lesions. Collagen will be digested with collagenase to release cells, which will be then assayed for apoptotic and other cellular expression markers by flow cytometry. This will provide information on host cell death and the activation profile of the immune cells due to the infection. An aliquot of the collagenase digest will be plated on Mueller-Hinton agar plates to determine the colony forming units (cfu) and hence survival and multiplication of the pathogen in the host cells, and the containment of the infection. Culture supernatants will be assayed for cytokine and antibody secretion. The cytokine profiles can be determined, for example, by a Bioplex assay and antibody responses can be examined, for example, by ELISA at different time points. For example, levels of IL-6, MCP-1, IL-12p35, IFNγ, IL-18, IP-10, and TNFα can be determined. IgM and IgG antibody ELISA can be conducted using culture supernatants to determine the levels of antibody production in response to the infection.

In another embodiment of the present invention, the infectious disease model can be used to test potential therapies that may cure the infection pre- and/or post-exposure. The model may also be used to address basic questions related to bacterial pathogenesis.

Studies with different types of TLR agonists and vaccine adjuvants have been conducted using the VS system. The protective effects of CpG and/or other adjuvants can readily be tested by pretreating the infection module with TLR agonists for 24-48 h, followed by introduction of the pathogen for 4-6 h. Infected APCs are taken out of the infection module and are then added the disease module for different periods. The collagenous matrix from disease module can be digested with collagenase. The protection offered by the adjuvants will be quantitated by plating the collagenase digest (as described above) and estimating the reduction in cfu.

As type I cytokines are important in control of initial infection (described above), extraneous IFNγ and/or IL-12 will be added in different concentrations to the disease module together with APCs from infection module. The control of infection will be studied in terms of reduction in cfu, by, for example, a plating method, and also the cytokine and antibody levels determined in culture supernatants.

The animal-type TTSS is important for *B. mallei* pathogenesis. This can be tested in the infection and disease module by using RD01 and RD02 mutant strains (Ribot & Ulrich (2006) Infect. Immun. 74, 4349-53).

Monoclonal antibodies have been produced against *B. mallei* and reported to passively protect Balb/c mice against *B. mallei* aerosol challenge (Treviño et al. (2006) Infect. Immun. 74, 1958-61). The protective effect of these monoclonals can be tested in the disease module system by adding protective or therapeutic antibodies to it. Infected APCs from the infection module together with protective antibodies and autologous PBMCs can be co-cast in the disease module for different periods. Protection by the antibodies is determined by reduction in cfu, by, for example, a plating method. Additionally, the antibodies in the culture supernatants in the disease module, produced in response to the infection, can be added to a new infection set and any protection offered can be determined in terms of reduction in cfu, by, for example, a plating method.

Vaccine candidates can be tested in the disease model by placing in vitro-immunized lymphocytes in the disease module. First, the vaccine is placed in the VS module to prime APCs. These APCs are then placed in the LTE module to prime lymphocytes, which are then used in the disease module. These in vitro-immunized lymphocytes are placed in the disease module along with infected APCs (obtained from a parallel infection with *B. mallei* in the IS module). Autologous PBMCs are used throughout. The protection offered is quantitated by reduction in bacterial cfu, by, for example, a plating method.

In another embodiment of the present invention, the disease model can be used to test new drug, vaccine, or therapeutic candidates for their efficacy against glanders or melioidosis, diseases caused by *Burkholderia mallei* and *B. pseudomallei*.

Example 18

HIV models. HIV (human immunodeficiency virus) is the virus that causes AIDS (acquired immune deficiency syndrome). In vivo, HIV-1 infects DCs and they move to the lymph nodes where the virus infects $CD4^+$ T cells. The lymph node then becomes the principal site of virus production. In embodiments of the present invention, the steps of this process are modeled by the modules of the artificial immune system.

In an embodiment of the present invention, HIV vaccine candidates are tested. As an example, HIV gp120 or gp140 vaccines can be assessed. HIV gp120/gp140-specific responses are assessed using PBMCs from human blood donors. First, the candidate vaccine is placed in the VS module to prime APCs. These primed APCs are then placed in the LTE module to prime lymphocytes. The in vitro-immunized lymphocytes and antibodies generated in the LTE are placed in the disease module along with infected APCs (obtained from a parallel infection with HIV in the infection site module). Autologous PBMCs are used throughout. Any protection offered is quantitated by, for example, assessing inhibition of viral replication or cell lysis.

Preparation of the infection site (IS) module involves growing a monolayer of endothelial cells over a collagen matrix. PBMCs are added on top of the endothelial cell layer. Monocytes preferentially extravasate across the endothelium into the collagen matrix with a small number of T and B cells (~5-10%). The monocytes in the PBMCs differentiate into APCs of a range of phenotypes as they traverse the endothelium. Some monocytes differentiate into mature and immature dendritic cells (DCs) and reverse transmigrate across the endothelium from the collagen, while other monocytes differentiate into macrophages and these sub-endothelial cells remain in the collagen matrix. The system mimics the in vivo differentiation process whereby antigen-presenting cells (e.g., monocytes) entering the site of infection receive differentiation signals as they cross the endothelium into the tissue. This method is superior to the widely used cytokine-induced (e.g., GM-CSF, IL-4, MCSF) methods of generating DCs and macrophages from PBMCs.

In an embodiment of the present invention, infectious virions can be added on top of the endothelial cells. HIV will infect the antigen-presenting cells. Thus, the IS module of the artificial immune system of the present invention closely mimics the in vivo scenario of infection; all of the components involved in the infection process, including endothelial cells, DCs, macrophages and lymphocytes, are present in the model system. Infected APCs can then be transferred to the LTE module.

The system can be incubated for different time periods to study progression of disease. Cytokine profiles can be assessed using a Bioplex assay and antibody responses can be assessed by ELISA at different time points using culture supernatants. For example, levels of IFNα, IFN-γ, IL-18, IL-6, MCP-1, MIP-1a, MIP-1b, IFN-β, and TNF-α will be determined.

To assess the efficacy of HIV vaccines, PBMC cells from a series of human blood donors are incubated with different concentrations (e.g., ~1-50 μg/mL) of HIV vaccine in the VS module and in a simple collagenous 3D matrix and are incubated for different time periods. The vaccine formulation will be taken up by monocytes, in a similar way to infectious virions, resulting in the establishment of a host immune response to the vaccine antigens. This host immune response to the test vaccine is then assessed in terms of, for example, cytokine responses, using for example, the Bioplex 22-cytokine kit. For examples, levels of IL-6, MCP-1, MIP-1a, MIP-1b, IFNβ, IFNγ, IL-18, and TNFα are determined. IgM and IgG antibody ELISAs are conducted with culture supernatants to determine the levels of antibody production in response to the test vaccine. If the LTE comprises a collagen matrix, the collagenous construct is digested with collagenase to release the cells and the activation and apoptotic state of T cells, B cells, and monocytes, macrophages, and dendritic cells in response to infection are determined by FACS analysis. Experiments using vectors expressing different viral proteins, peptides, and combinations of proteins can also be used to assess differences and variations in the host immune responses to viral proteins.

In the IS, PBMCs are infected by adding HIV at different multiplicities of infection (MOI) on top of the endothelial cells. HIV infects antigen-presenting cells in the IS. These infected APCs are then transferred to the disease module/LTE module described above where they are added with autologous PBMCs and can be co-cast in collagen. The lymphocytes mount an immune response against the pathogen. The system can be incubated for different time periods to study disease progression. The disease manifestation is observed in terms of measurable events or parameters, such as development of macrophages and lymphocytes death and the host immune response to contain the infection. Containment of infection will be reflected as a reduction in viral counts. Host macrophages, DCs, and lymphocytes will secrete proinflammatory cytokines and chemokines and also antibodies in response to the infection; these can also be assayed in culture supernatants.

The cytokine profiles can be determined, for example, by a Bioplex assay and antibody responses can be examined, for example, by ELISA at different time points. For example, levels of IL-6, MCP-1, IL-12p35, IFNγ, IL-18, IP-10, and TNFα can be determined. IgM and IgG antibody ELISA can be conducted using culture supernatants to determine the levels of antibody production in response to the infection.

In an embodiment of the present invention, diseased cells (e.g., HIV-infected APCs) would be exposed to 'output' from the VS/LTE combination—either by transferring VS/LTE 'output' (FIG. 11) or by putting the diseased cells (e.g., HIV-infected APCs) into the LTE (FIG. 12), in both cases, to evaluate the effect on the diseased cells. The effects on the LTE components by the diseased cells can be assessed, as can any effect on the diseased cells.

In an embodiment of the invention, IS-derived cells would be infected before putting them into a naïve (uninfected) LTE, to assess the effects on the cells of the LTE. This models cells becoming infected in the periphery before moving to the lymph node (or LTE). Effects on the LTE components by the diseased cells can be assessed, as can effects on the diseased cells.

In another embodiment of the present invention, a naive (uninfected) LTE is infected to assess the effects on cells of the LTE.

While the foregoing specification teaches the principles of the present invention, with examples provided for the purpose of illustration, it will be appreciated by one skilled in the art from reading this disclosure that various changes in form and detail can be made without departing from the true scope of the invention.

Any and all materials cited or referred to herein, including, but not limited to, books, manuals, journal articles, abstracts, posters, websites, product literature, and other publications of any type is hereby expressed incorporated by reference in its entirety.

What is claimed is:

1. An in vitro two culture cellular system comprising:
   a culture of a two- or three-dimensional matrix, comprising lymphoid tissue; and
   a culture of diseased cells, wherein said diseased cells are immune system cells, selected from the group consisting of PBMCs, monocytes, macrophages, dendritic cells, lymphocytes, and antigen-presenting cells.

2. The in vitro system of claim 1, wherein said diseased cells are selected from the group consisting of virally infected cells, bacterially infected cells, tumor cells, and autoimmune disease-afflicted cells.

3. The in vitro system of claim 1, wherein said diseased cells are virally infected cells.

4. The in vitro system of claim 1, wherein said diseased cells are bacterially infected cells.

5. The in vitro system of claim 1, wherein said diseased cells comprise PBMCs derived from blood donors infected with a virus.

6. The in vitro system of claim 1, wherein said diseased cells comprise PBMCs derived from uninfected blood donors, and wherein said PBMCs are in vitro with a virus.

7. The in vitro system of claim 1, wherein said diseased cells comprise PBMCs derived from blood donors infected with a bacterium.

8. The in vitro system of claim 1, wherein said diseased cells comprise PBMCs derived from blood donors afflicted with an autoimmune disease.

9. The in vitro system of claim 1, wherein said diseased cells comprise PBMCs derived from uninfected blood donors, and wherein said PBMCs are infected in vitro with a bacterium.

10. An in vitro three culture cellular system comprising:
    a culture of a two- or three-dimensional matrix, comprising lymphoid tissue;
    a culture of a two- or three-dimensional matrix, comprising epithelial and/or endothelial cells; and
    a culture of diseased cells, wherein said diseased cells are immune system cells, selected from the group consisting of PBMCs, monocytes, macrophages, dendritic cells, lymphocytes, and antigen-presenting cells.

11. The in vitro system of claim 10, wherein said diseased cells are selected from the group consisting of virally infected cells, bacterially infected cells, tumor cells, and autoimmune disease-afflicted cells.

12. The in vitro system of claim 10, wherein said diseased cells are virally infected cells.

13. The in vitro system of claim 10, wherein said diseased cells are bacterially infected cells.

14. The in vitro system of claim 10, wherein said diseased cells comprise PBMCs derived from blood donors infected with a virus.

15. The in vitro system of claim 10, wherein said diseased cells comprise PBMCs derived from uninfected blood donors, and wherein said PBMCs are infected in vitro with a virus.

16. The in vitro system of claim 10, wherein said diseased cells comprise PBMCs derived from blood donors infected with a bacterium.

17. The in vitro system of claim 10, wherein said diseased cells comprise PBMCs derived from blood donors afflicted with an autoimmune disease.

18. The in vitro system of claim 10, wherein said diseased cells comprise PBMCs derived from uninfected blood donors, and wherein said PBMCs are infected in vitro with a bacterium.

* * * * *

UNITED STATES PATENT AND TRADEMARK OFFICE
CERTIFICATE OF CORRECTION

PATENT NO. : 7,771,999 B2  Page 1 of 1
APPLICATION NO. : 12/047107
DATED : August 10, 2010
INVENTOR(S) : William L. Warren et al.

It is certified that error appears in the above-identified patent and that said Letters Patent is hereby corrected as shown below:

The following heading and paragraph are being inserted in column 1, at line 3:

--STATEMENT REGARDING FEDERALLY SPONSORED RESEARCH

This invention was made with government support under contract number NBCHC060058, awarded by the Defense Advanced Research Projects Agency, issued by the U.S. Army Medical Research Acquisition Activity, and administered by the U.S. Department of the Interior-National Business Center. The government has certain rights in the invention.--

Signed and Sealed this

Fourteenth Day of September, 2010

David J. Kappos
*Director of the United States Patent and Trademark Office*